(12) United States Patent
Berger et al.

(10) Patent No.: US 8,858,636 B2
(45) Date of Patent: Oct. 14, 2014

(54) INTERVERTEBRAL IMPLANT

(75) Inventors: Roger Berger, Oberdorf (CH); Joern Richter, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 47 days.

(21) Appl. No.: 12/757,443

(22) Filed: Apr. 9, 2010

(65) Prior Publication Data

US 2011/0251690 A1     Oct. 13, 2011

(51) Int. Cl.
*A61F 2/44* (2006.01)
*A61F 2/30* (2006.01)

(52) U.S. Cl.
CPC ..... *A61F 2/4425* (2013.01); *A61F 2310/00029* (2013.01); *A61F 2002/30848* (2013.01); *A61F 2310/00796* (2013.01); *A61F 2310/00017* (2013.01); *A61F 2002/30843* (2013.01); *A61F 2310/00179* (2013.01); *A61F 2002/30275* (2013.01); *A61F 2002/30772* (2013.01); *A61F 2002/30387* (2013.01); *A61F 2002/30787* (2013.01); *A61F 2002/30504* (2013.01); *A61F 2002/30649* (2013.01); *A61F 2002/3093* (2013.01); *A61F 2002/443* (2013.01); *A61F 2/3094* (2013.01); *A61F 2002/30273* (2013.01); *A61F 2002/30563* (2013.01); *A61F 2002/30841* (2013.01); *A61F 2002/30616* (2013.01); *A61F 2002/30326* (2013.01); *A61F 2310/00023* (2013.01)
USPC ..................................... 623/17.15

(58) Field of Classification Search
CPC .............. A61F 2/4425; A61F 2002/30772; A61F 2002/30841
USPC ............................. 623/17.11–17.16; 606/297
See application file for complete search history.

(56) References Cited

U.S. PATENT DOCUMENTS

| | | | |
|---|---|---|---|
| 2,549,731 A | 4/1951 | Wattley | |
| 4,877,020 A | 10/1989 | Vich | |
| 4,997,432 A | 3/1991 | Keller | |
| 5,071,437 A * | 12/1991 | Steffee | 623/17.16 |
| 5,443,514 A | 8/1995 | Steffee | |
| 5,522,899 A | 6/1996 | Michelson | |
| 5,676,701 A | 10/1997 | Yuan et al. | |
| 5,888,227 A * | 3/1999 | Cottle | 623/17.16 |
| 6,066,174 A | 5/2000 | Farris | |

(Continued)

FOREIGN PATENT DOCUMENTS

| | | |
|---|---|---|
| EP | 1587461 B1 | 4/2008 |
| WO | WO 00/49977 A1 | 8/2000 |
| WO | WO 2007/038611 A2 * | 4/2007 |
| WO | WO 2011/126490 A1 | 10/2011 |

OTHER PUBLICATIONS

International Patent Application No. PCT/US2010/030523: International Search Report and Written Opinion dated Jan. 12, 2011.

*Primary Examiner* — Ellen C Hammond
*Assistant Examiner* — Jacqueline Johanas
(74) *Attorney, Agent, or Firm* — Baker & Hostetler LLP

(57) ABSTRACT

An intervertebral implant includes opposing upper and lower endplates that are configured to engage respective vertebral surfaces in an intervertebral space. The implant carries a plurality of bone fixation spikes that extend out from each endplate. The spikes define a plurality of outer surfaces that extend from a base to a tip. The spikes are laterally staggered, and have a height that increases along a longitudinal direction from the front toward the rear of the implant, and a define recess formed in at least one outer surfaces.

23 Claims, 22 Drawing Sheets

(56) References Cited

U.S. PATENT DOCUMENTS

| | | | |
|---|---|---|---|
| 6,159,215 A | 12/2000 | Urbahns et al. | |
| 6,319,257 B1 | 11/2001 | Carignan et al. | |
| 6,416,551 B1 | 7/2002 | Keller | |
| 6,440,168 B1* | 8/2002 | Cauthen | 623/17.14 |
| 6,517,580 B1* | 2/2003 | Ramadan et al. | 623/17.15 |
| 6,740,118 B2 | 5/2004 | Eisermann et al. | |
| 6,827,740 B1 | 12/2004 | Michelson | |
| 6,936,071 B1 | 8/2005 | Marnay et al. | |
| 6,966,929 B2 | 11/2005 | Mitchell | |
| 6,994,727 B2 | 2/2006 | Khandkar et al. | |
| 7,051,417 B2 | 5/2006 | Michelson | |
| 7,105,024 B2 | 9/2006 | Richelsoph | |
| 7,115,143 B1 | 10/2006 | Michelson | |
| 7,166,129 B2 | 1/2007 | Michelson | |
| 7,198,644 B2 | 4/2007 | Schultz et al. | |
| 7,204,852 B2 | 4/2007 | Marnay et al. | |
| 7,217,292 B2 | 5/2007 | Ralph et al. | |
| 7,235,103 B2 | 6/2007 | Rivin | |
| 7,244,275 B2 | 7/2007 | Michelson | |
| 7,273,496 B2 | 9/2007 | Mitchell | |
| 7,300,465 B2* | 11/2007 | Paul et al. | 623/17.11 |
| 7,331,995 B2 | 2/2008 | Eisermann et al. | |
| 7,364,589 B2 | 4/2008 | Eisermann | |
| 7,442,211 B2 | 10/2008 | Villiers et al. | |
| 7,517,363 B2 | 4/2009 | Rogers | |
| 7,563,286 B2* | 7/2009 | Gerber et al. | 623/17.14 |
| 7,594,919 B2 | 9/2009 | Peterman | |
| 7,618,423 B1 | 11/2009 | Valentine et al. | |
| 7,686,809 B2 | 3/2010 | Triplett et al. | |
| 7,850,736 B2* | 12/2010 | Heinz | 623/17.16 |
| 7,891,434 B2 | 2/2011 | Gaudette et al. | |
| 8,142,435 B2 | 3/2012 | Refai et al. | |
| 8,197,484 B2 | 6/2012 | Sato et al. | |
| 8,235,997 B2 | 8/2012 | Hoffman et al. | |
| 8,486,081 B2 | 7/2013 | Parsons et al. | |
| 2004/0147937 A1 | 7/2004 | Dunbar et al. | |
| 2004/0172133 A1* | 9/2004 | Gerber et al. | 623/17.11 |
| 2004/0254643 A1* | 12/2004 | Jackson | 623/17.11 |
| 2005/0021042 A1 | 1/2005 | Marnay et al. | |
| 2005/0027362 A1* | 2/2005 | Williams et al. | 623/17.11 |
| 2005/0143749 A1 | 6/2005 | Zalenski et al. | |
| 2005/0240267 A1* | 10/2005 | Randall et al. | 623/17.11 |
| 2005/0251260 A1* | 11/2005 | Gerber et al. | 623/17.13 |
| 2006/0025777 A1 | 2/2006 | Weber | |
| 2006/0030860 A1 | 2/2006 | Peterman | |
| 2006/0074418 A1 | 4/2006 | Jackson | |
| 2006/0129241 A1* | 6/2006 | Boyer et al. | 623/17.15 |
| 2006/0235535 A1* | 10/2006 | Ferree et al. | 623/17.16 |
| 2006/0293690 A1 | 12/2006 | Abdelgany | |
| 2007/0010887 A1* | 1/2007 | Williams et al. | 623/17.15 |
| 2007/0072475 A1* | 3/2007 | Justin et al. | 439/354 |
| 2007/0073311 A1* | 3/2007 | Williams et al. | 606/108 |
| 2007/0093900 A1* | 4/2007 | Williams et al. | 623/17.11 |
| 2007/0100455 A1* | 5/2007 | Parsons | 623/17.14 |
| 2007/0112429 A1* | 5/2007 | Muhanna et al. | 623/17.15 |
| 2007/0123907 A1 | 5/2007 | Weber | |
| 2007/0156239 A1* | 7/2007 | Zipnick et al. | 623/17.11 |
| 2007/0255407 A1* | 11/2007 | Castleman et al. | 623/17.11 |
| 2007/0255414 A1 | 11/2007 | Melkent | |
| 2007/0255416 A1 | 11/2007 | Melkent | |
| 2007/0270956 A1* | 11/2007 | Heinz | 623/17.11 |
| 2007/0282441 A1* | 12/2007 | Stream et al. | 623/17.11 |
| 2007/0299521 A1* | 12/2007 | Glenn et al. | 623/17.11 |
| 2008/0015698 A1* | 1/2008 | Marino et al. | 623/17.15 |
| 2008/0103598 A1* | 5/2008 | Trudeau et al. | 623/17.16 |
| 2008/0200984 A1 | 8/2008 | Jodaitis et al. | |
| 2008/0255574 A1 | 10/2008 | Dye | |
| 2008/0275447 A1 | 11/2008 | Sato et al. | |
| 2008/0275455 A1 | 11/2008 | Berry et al. | |
| 2008/0287957 A1 | 11/2008 | Hester et al. | |
| 2008/0306488 A1 | 12/2008 | Altarac et al. | |
| 2008/0306557 A1 | 12/2008 | Altarac et al. | |
| 2009/0018661 A1* | 1/2009 | Kim et al. | 623/17.16 |
| 2009/0030421 A1 | 1/2009 | Hawkins et al. | |
| 2009/0030422 A1 | 1/2009 | Parsons et al. | |
| 2009/0216330 A1 | 8/2009 | Geisert et al. | |
| 2009/0228054 A1 | 9/2009 | Hoffman et al. | |
| 2009/0254182 A1 | 10/2009 | Kovarik et al. | |
| 2010/0023019 A1 | 1/2010 | Fuhrer et al. | |
| 2010/0023128 A1 | 1/2010 | Malberg et al. | |
| 2010/0057205 A1* | 3/2010 | Justin et al. | 623/17.15 |
| 2010/0121388 A1 | 5/2010 | Flickinger et al. | |
| 2010/0168803 A1 | 7/2010 | Hestad et al. | |
| 2010/0191241 A1 | 7/2010 | McCormick et al. | |
| 2010/0249795 A1 | 9/2010 | DiMauro et al. | |
| 2010/0268343 A1* | 10/2010 | Dewey et al. | 623/17.16 |
| 2010/0280618 A1 | 11/2010 | Jodaitis et al. | |
| 2010/0286784 A1 | 11/2010 | Curran et al. | |
| 2010/0331901 A1 | 12/2010 | Iott et al. | |
| 2011/0015678 A1 | 1/2011 | Jackson | |
| 2011/0301612 A1 | 12/2011 | Berger et al. | |
| 2012/0150241 A1 | 6/2012 | Ragab et al. | |

* cited by examiner

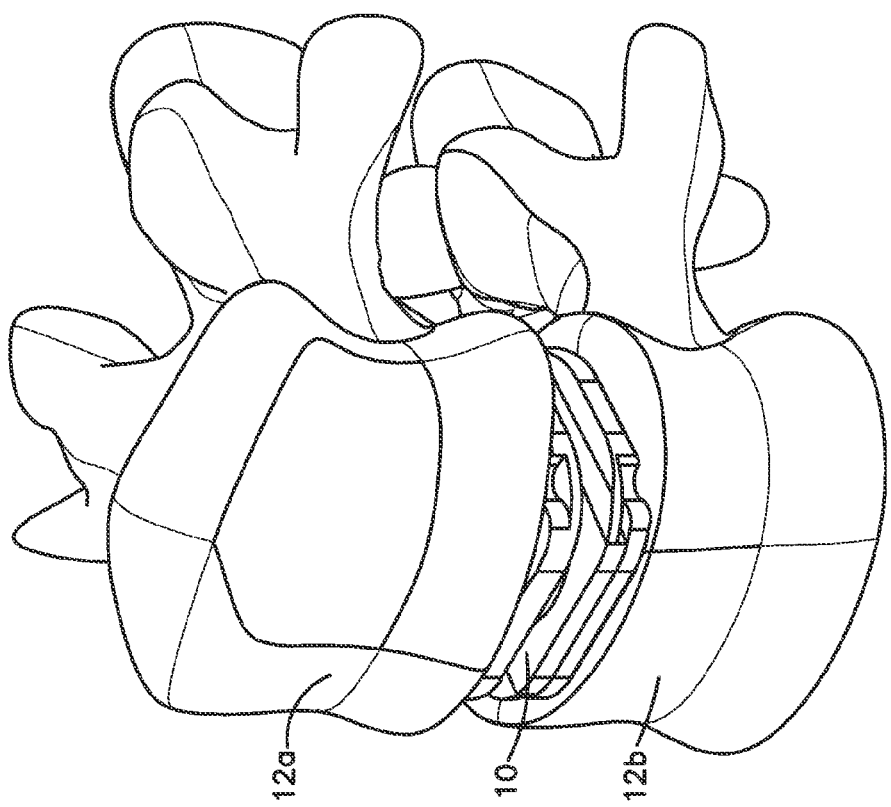
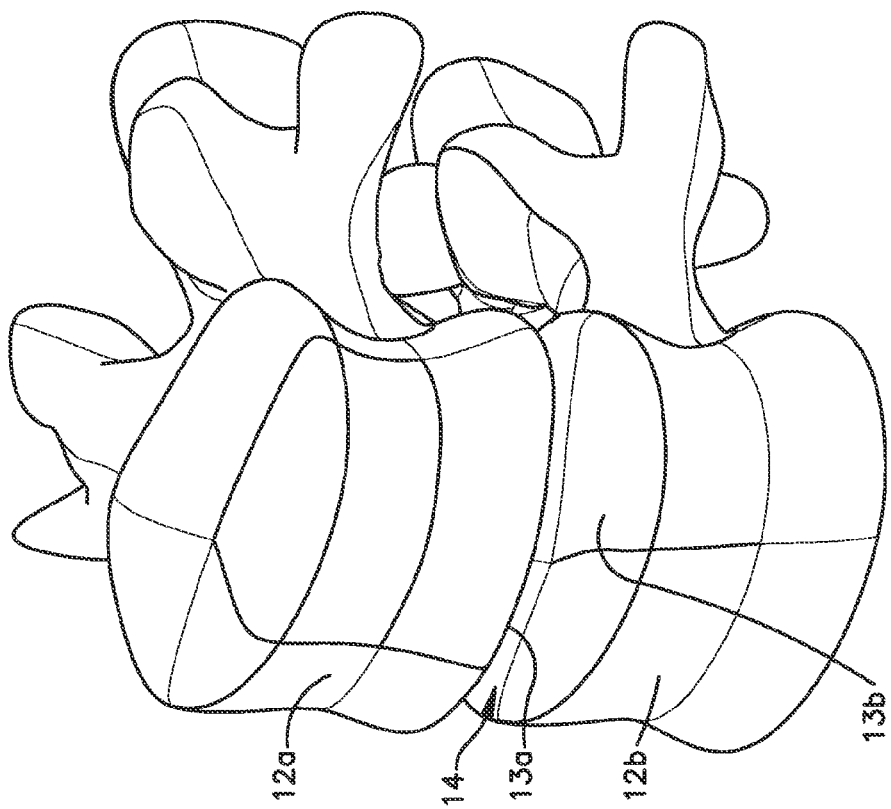

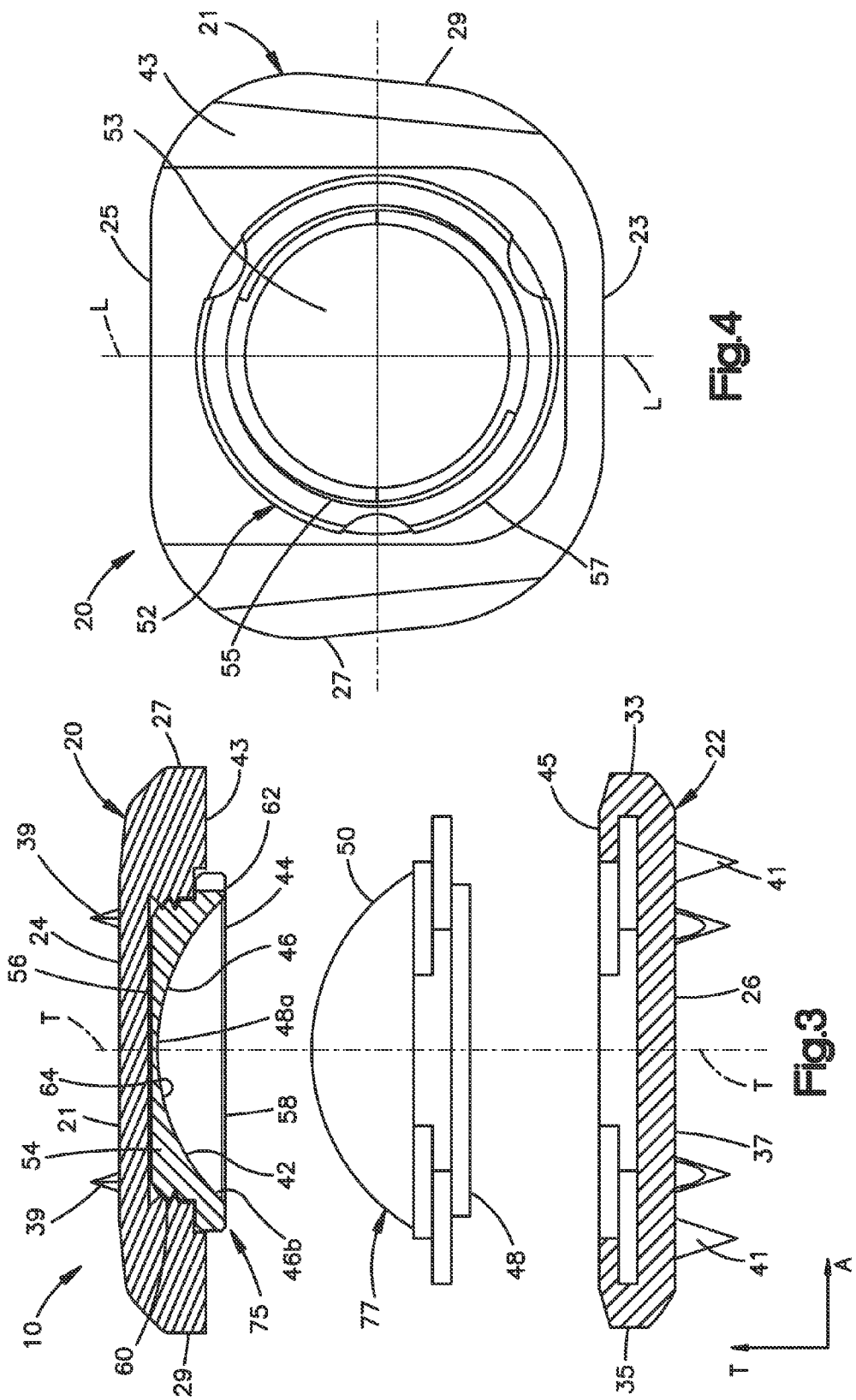

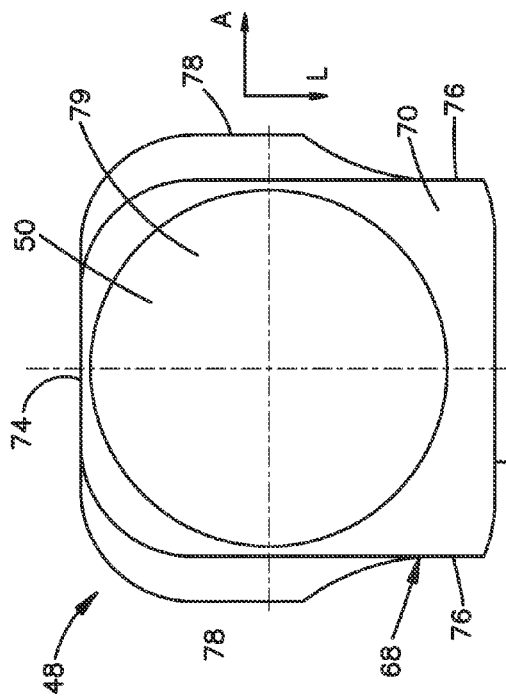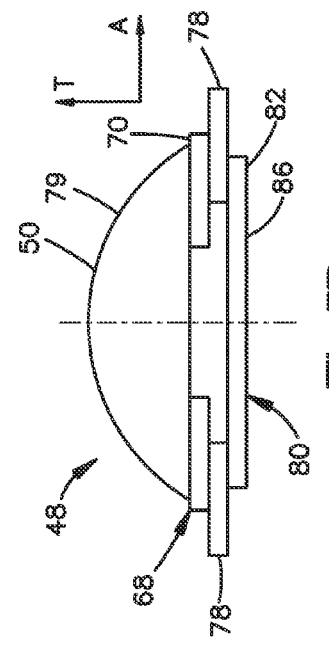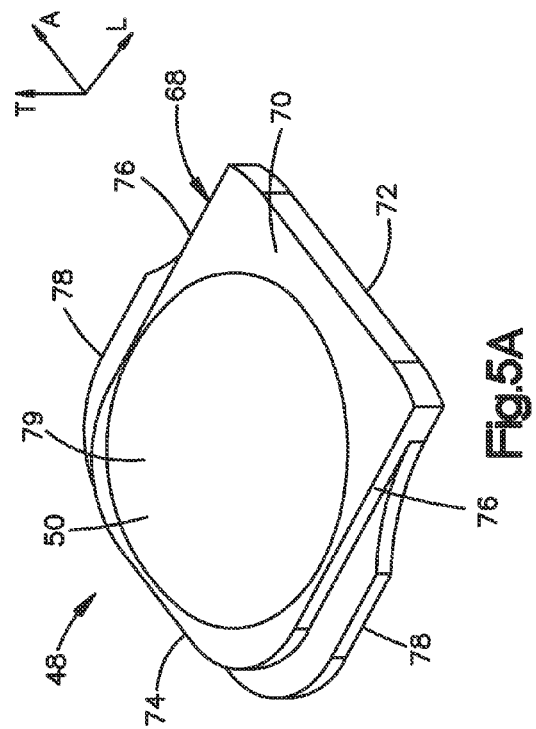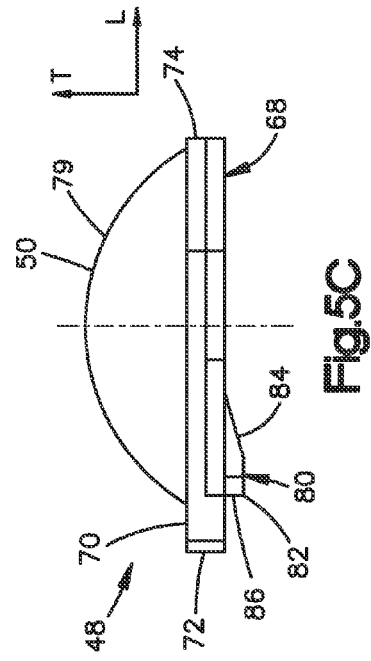

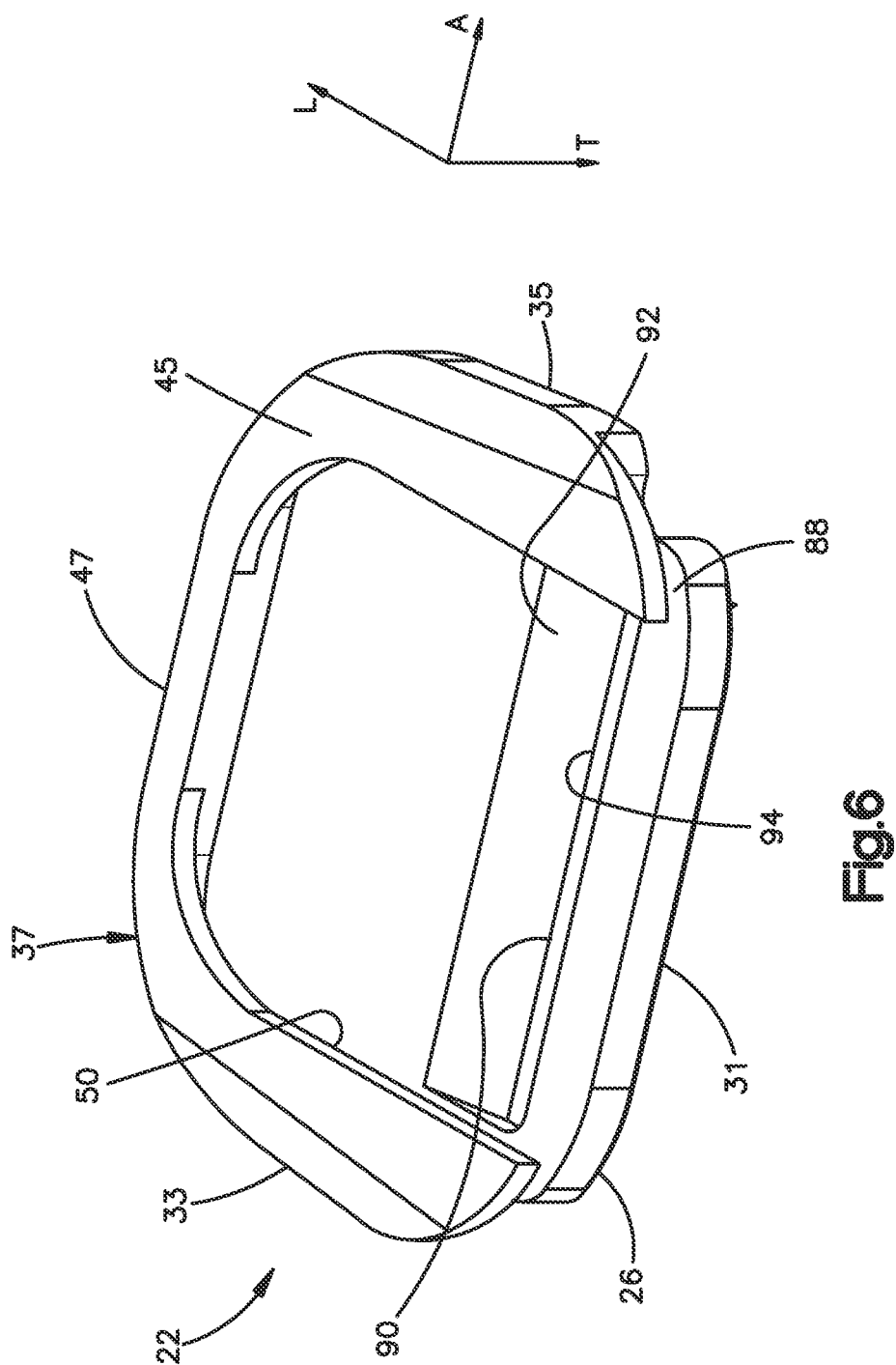

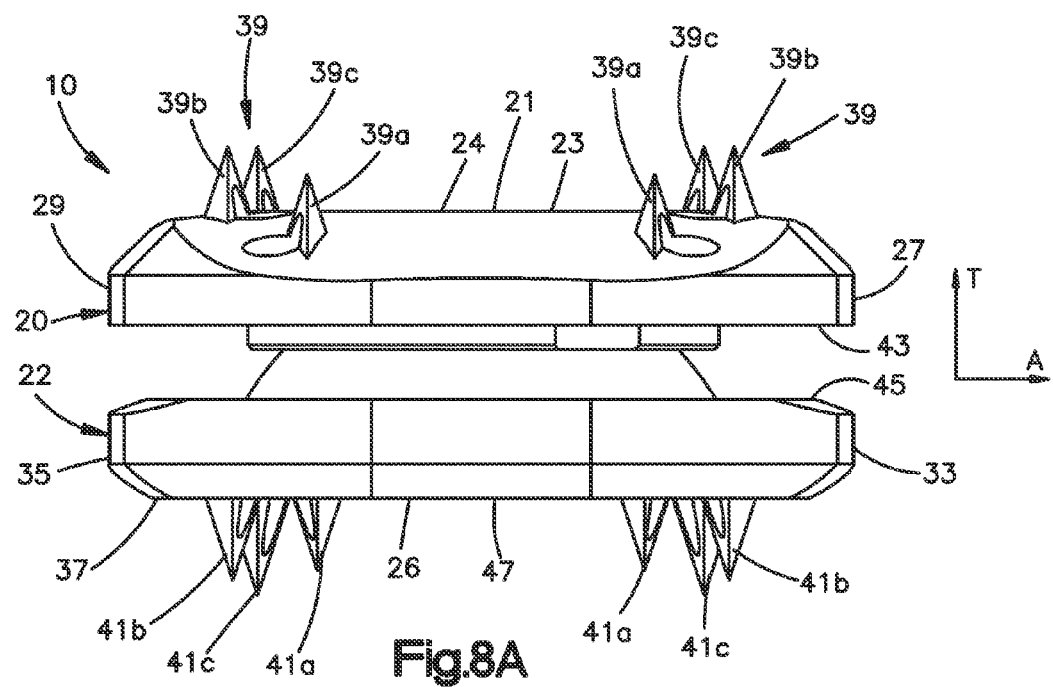
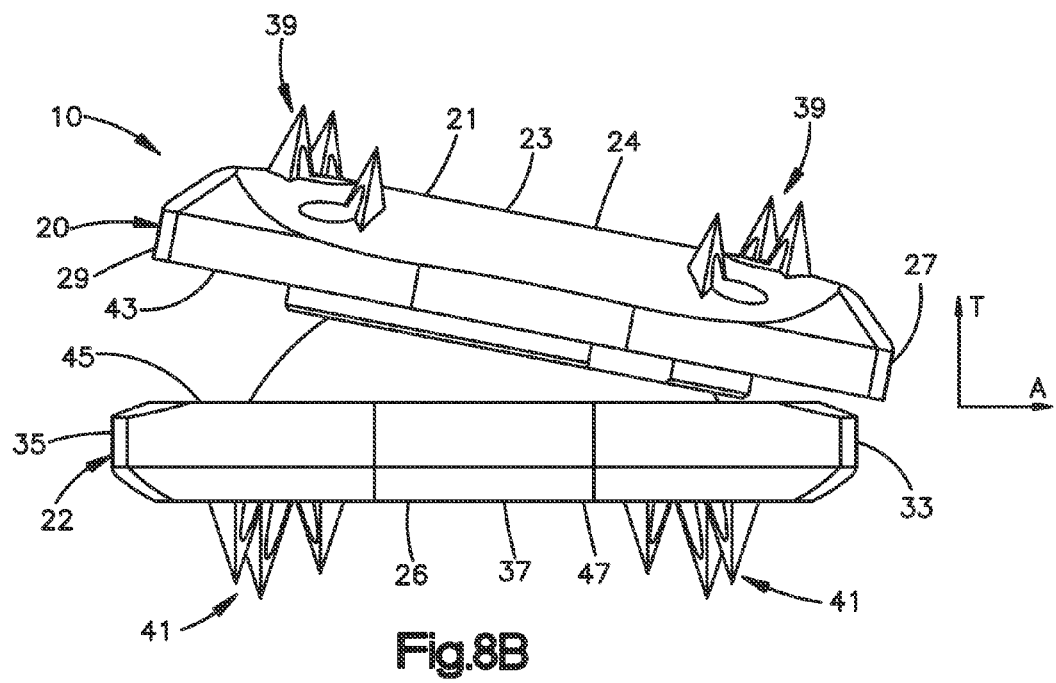

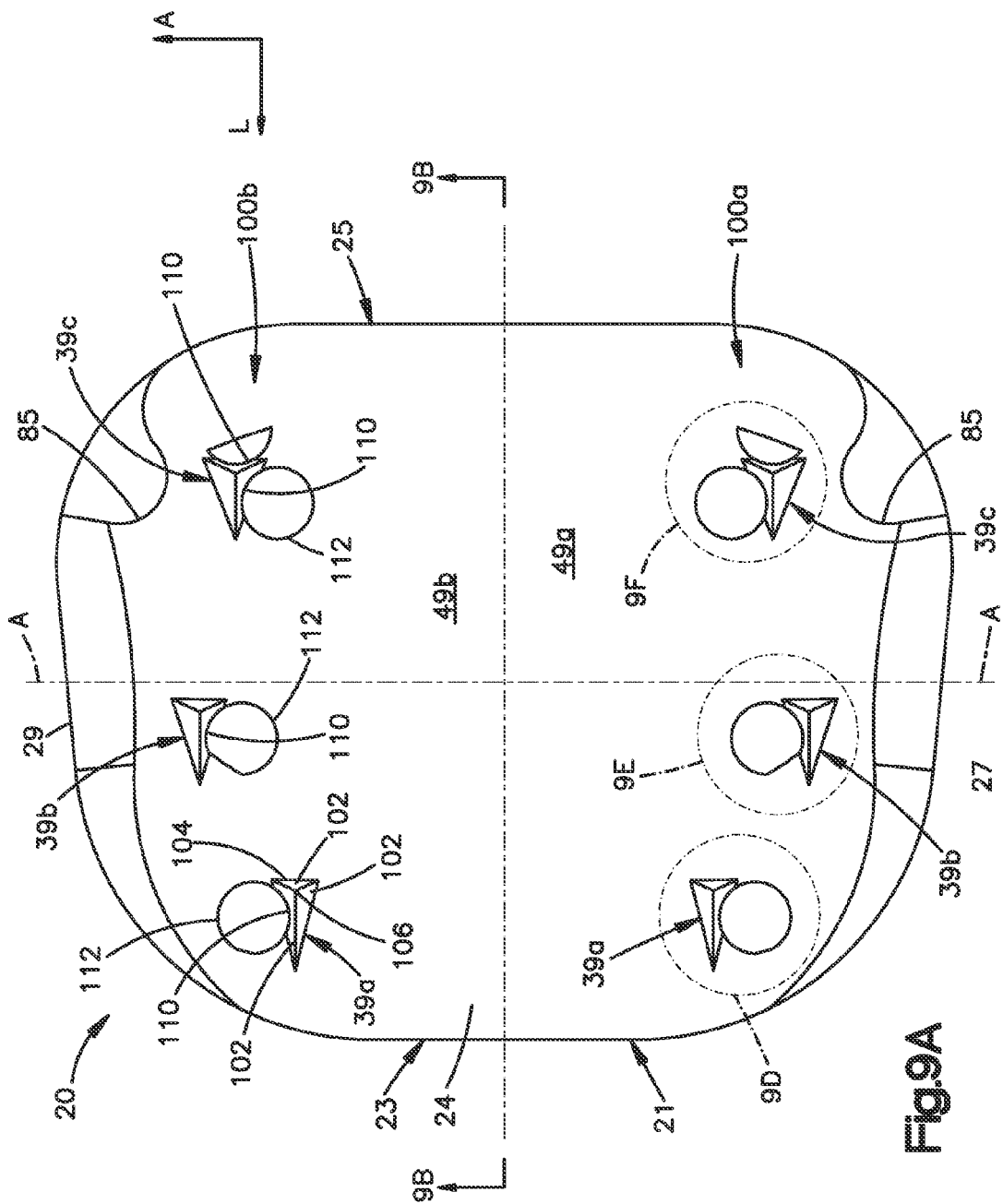

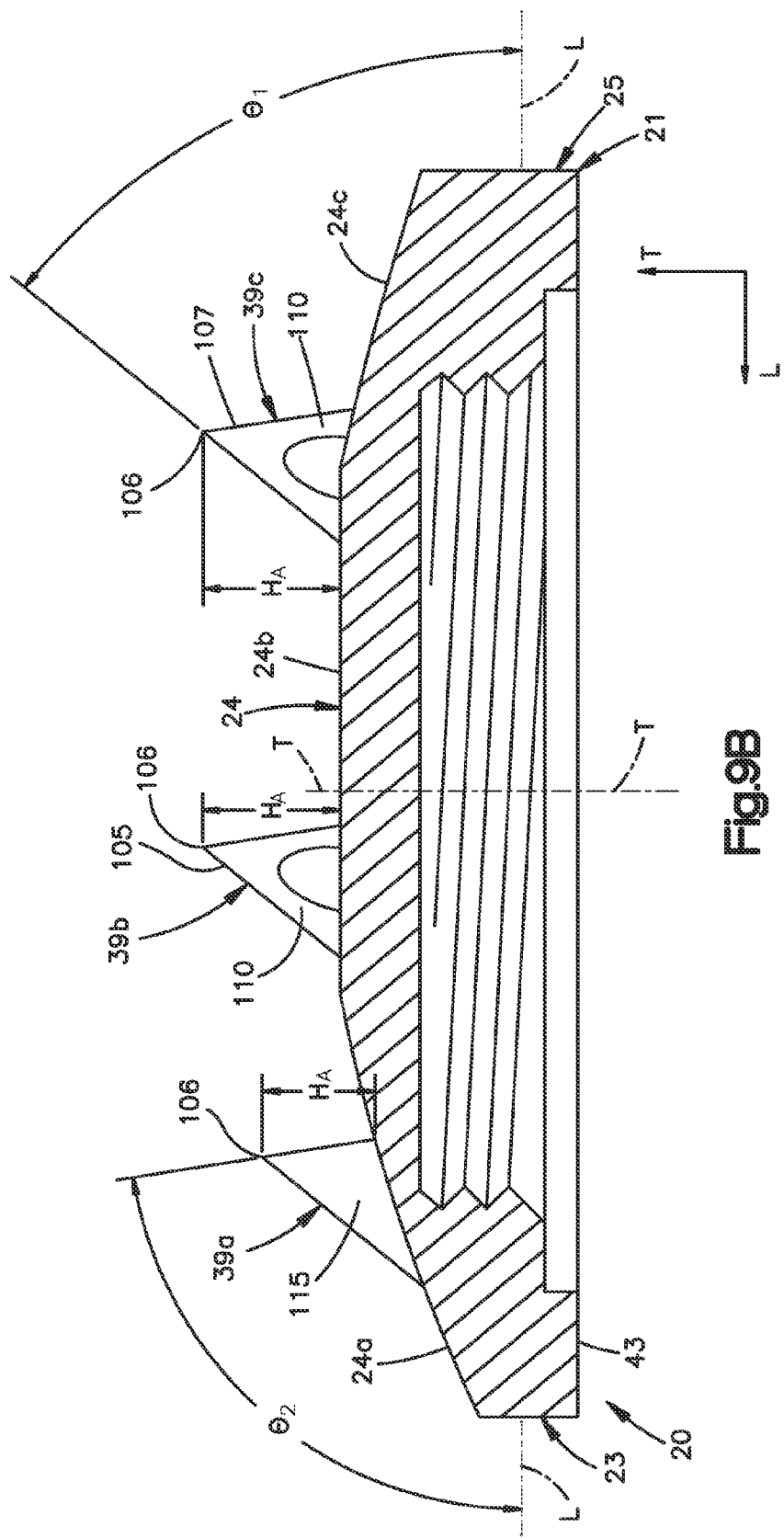

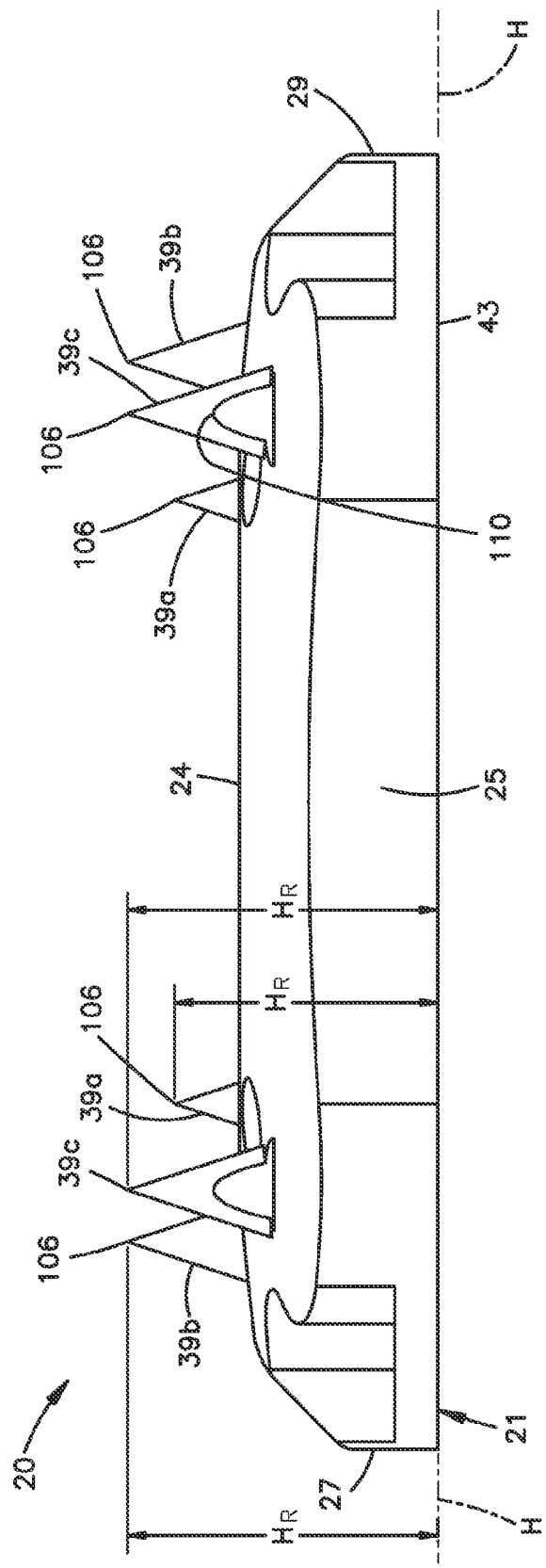

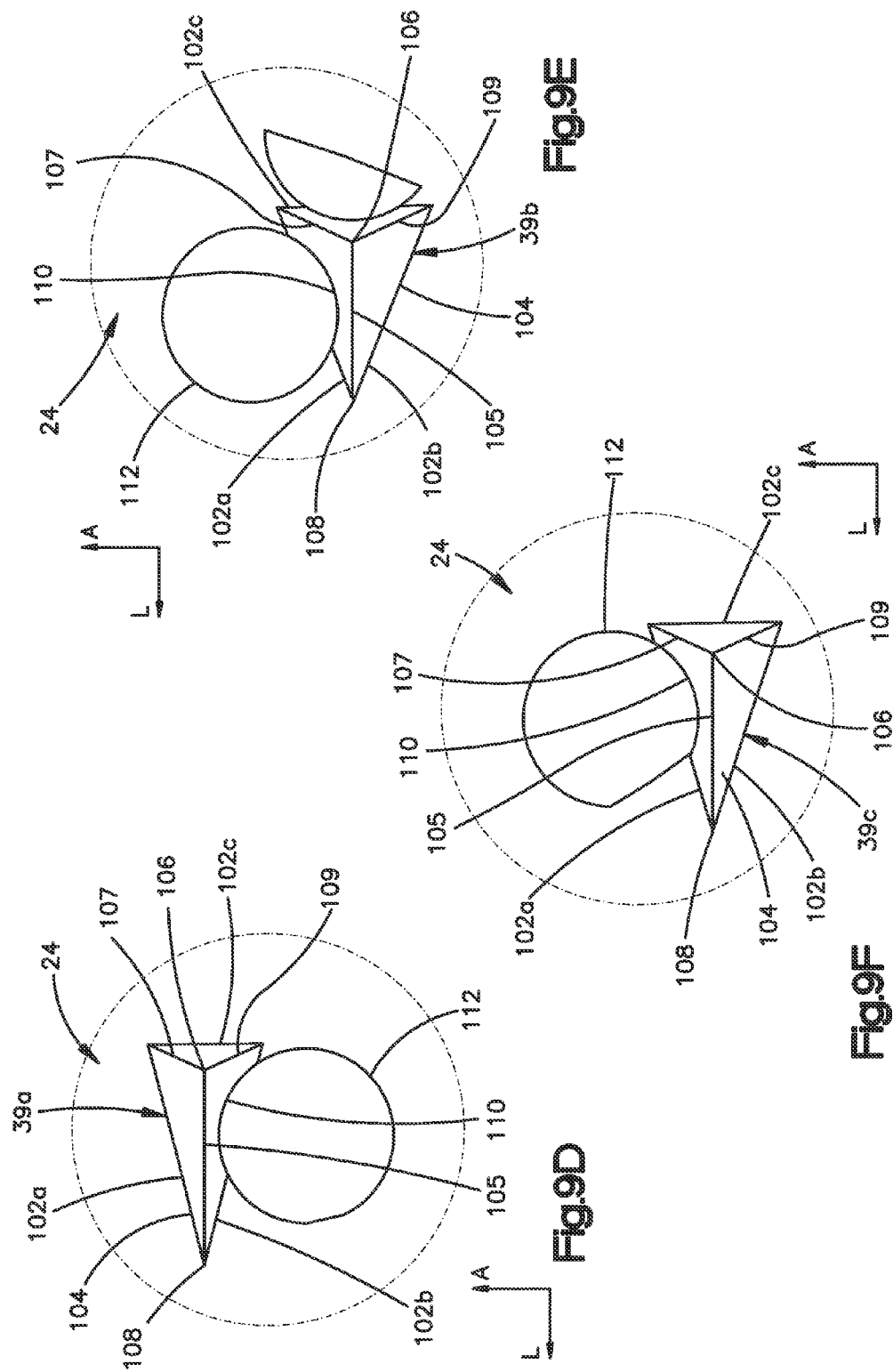

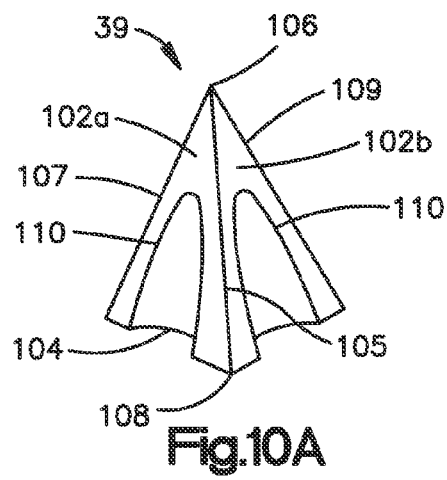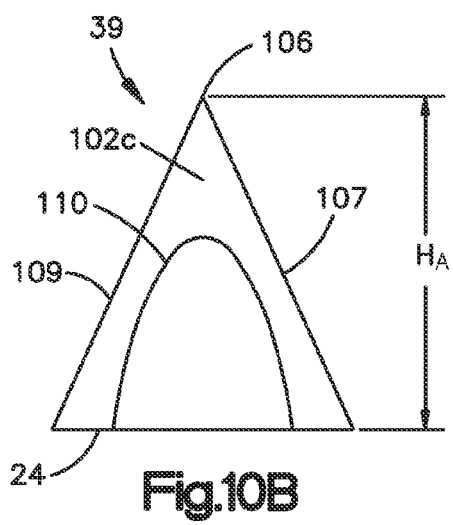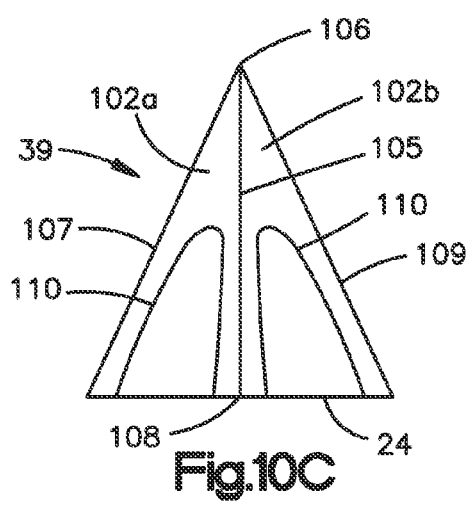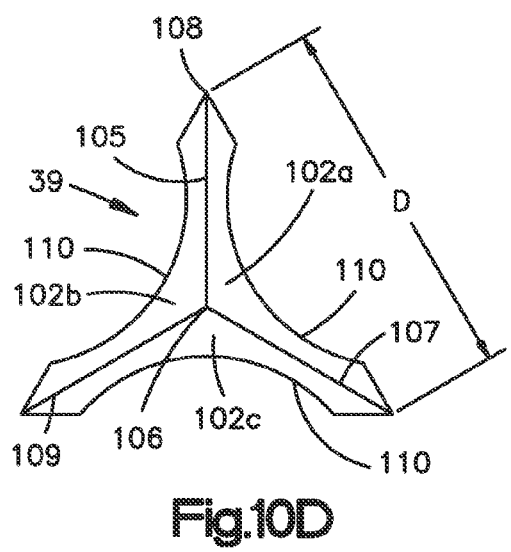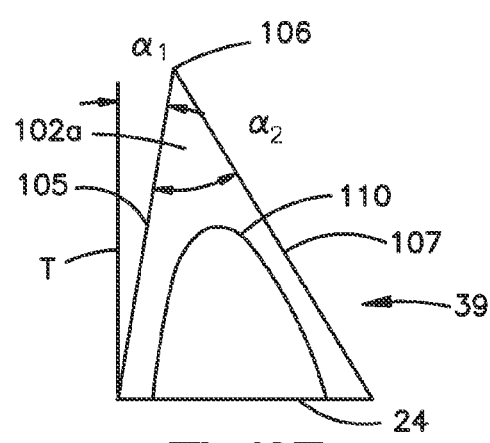

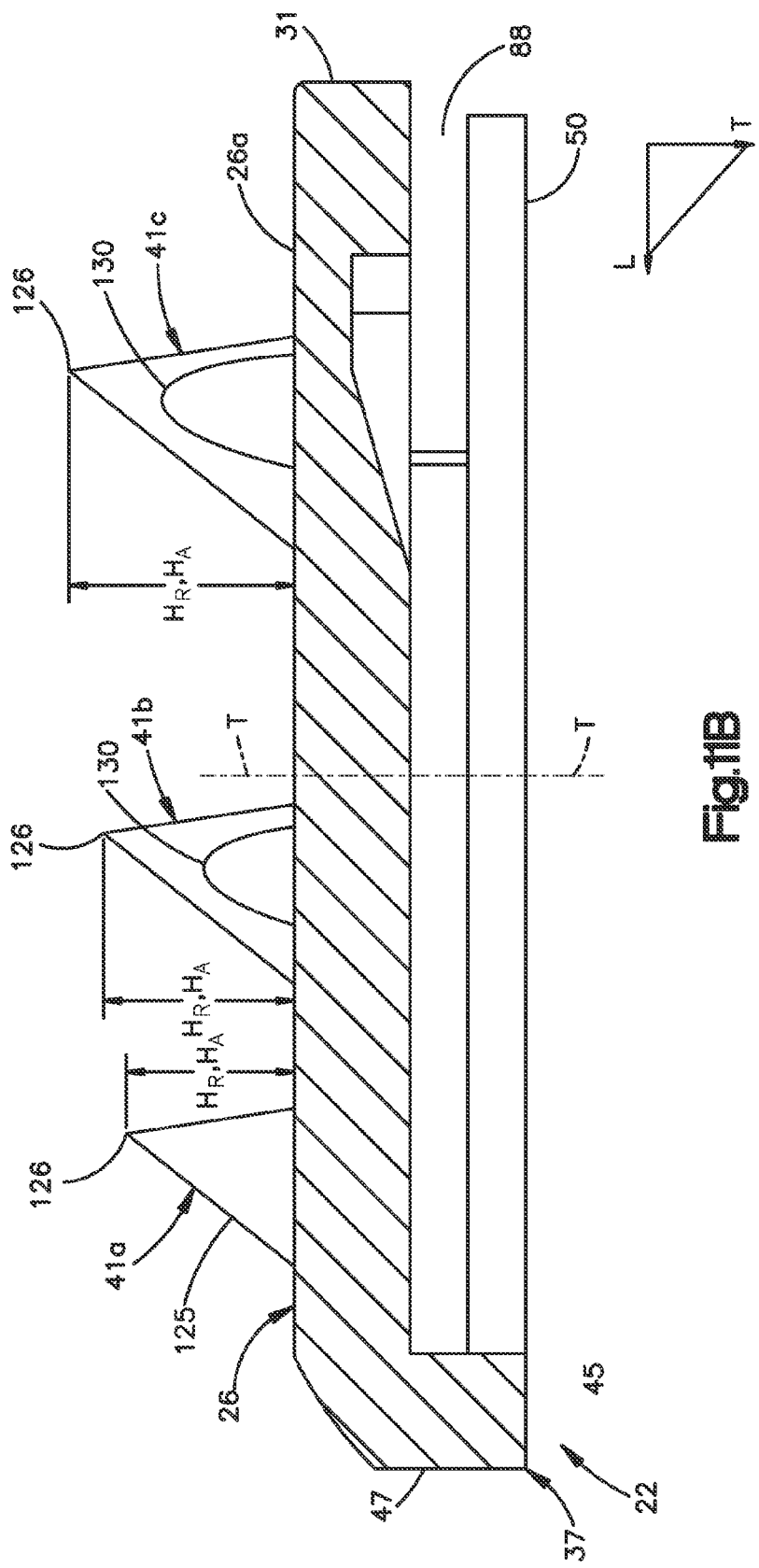

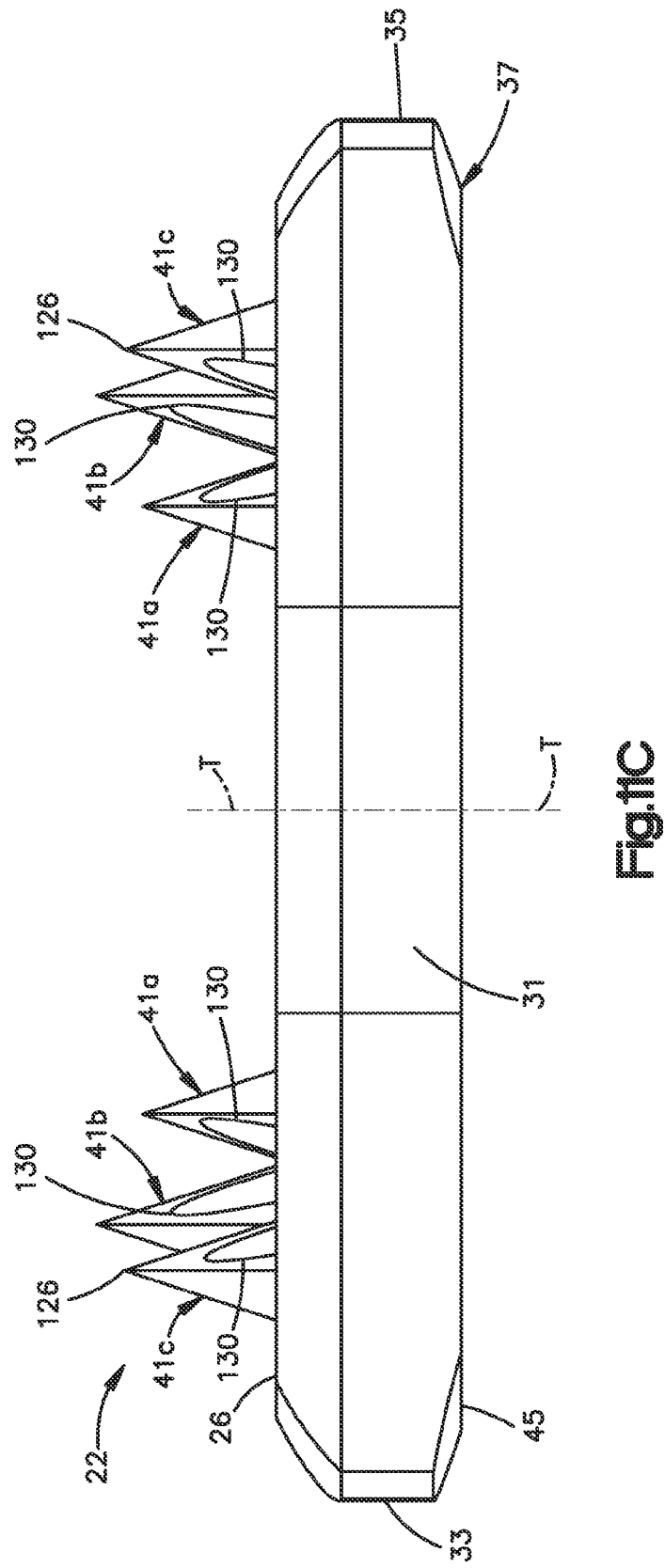

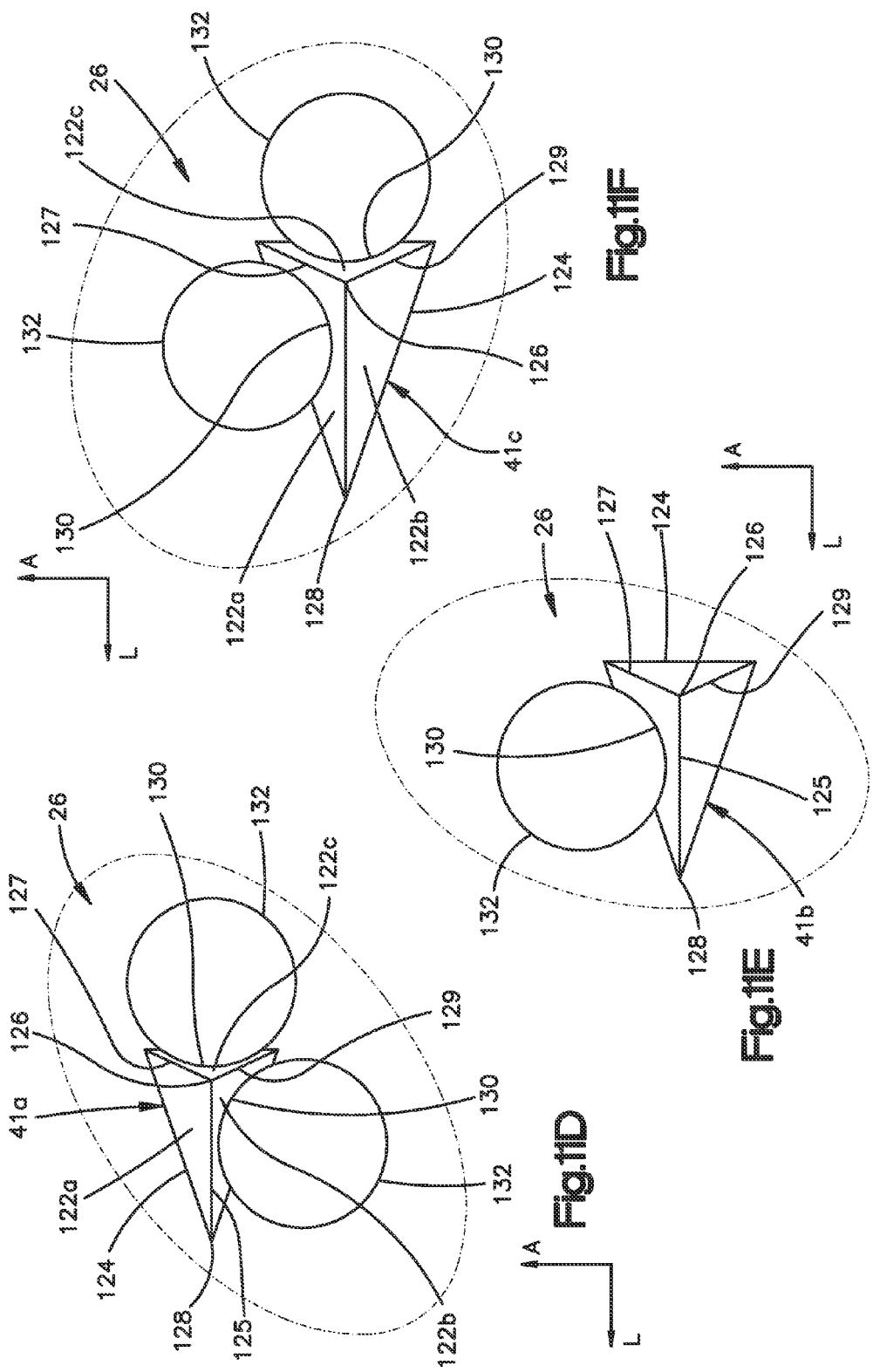

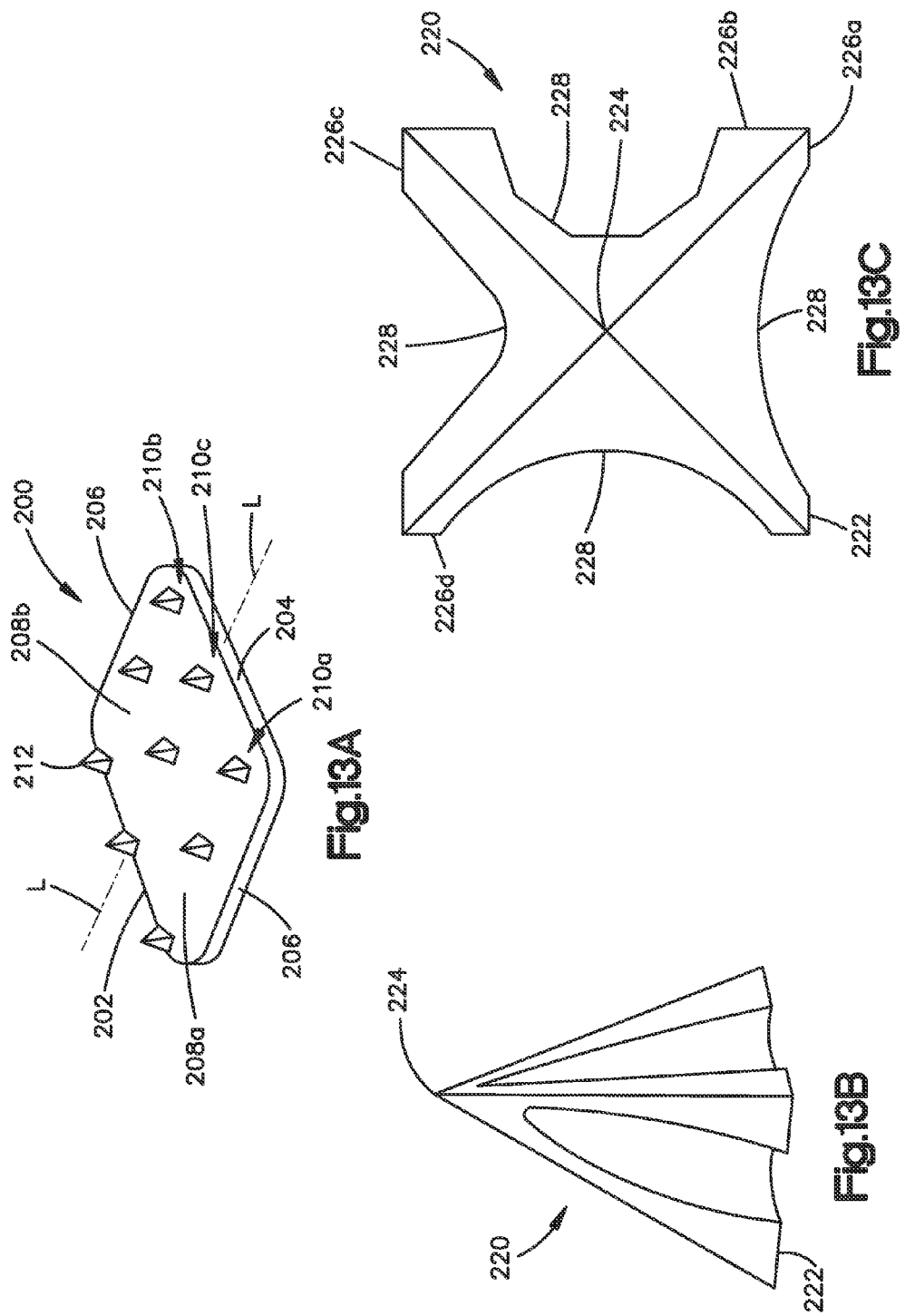

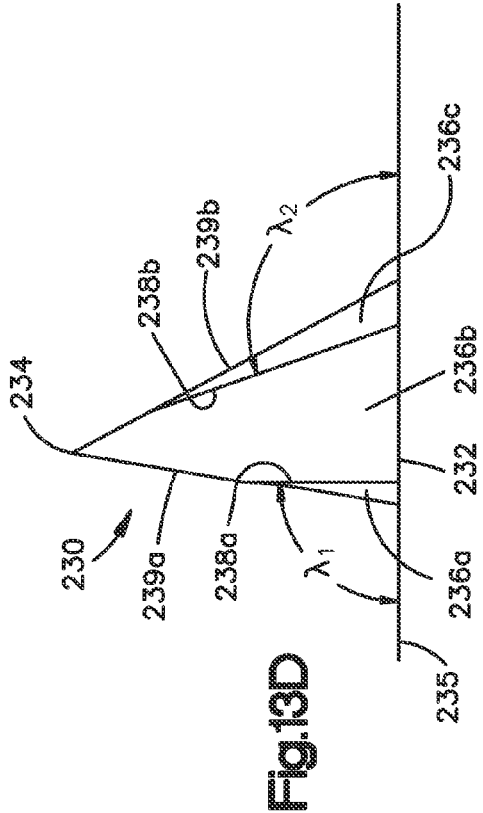
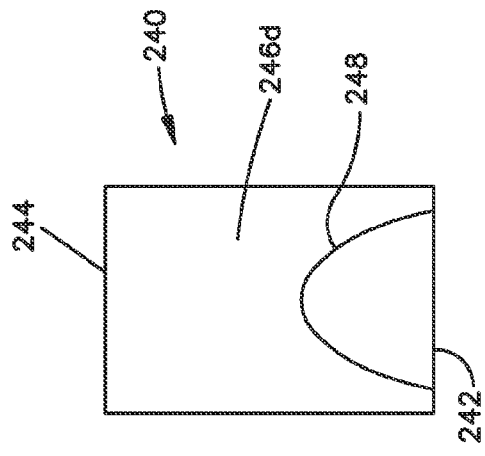
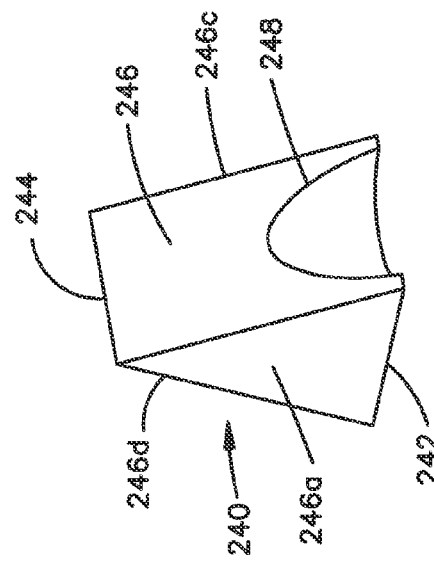

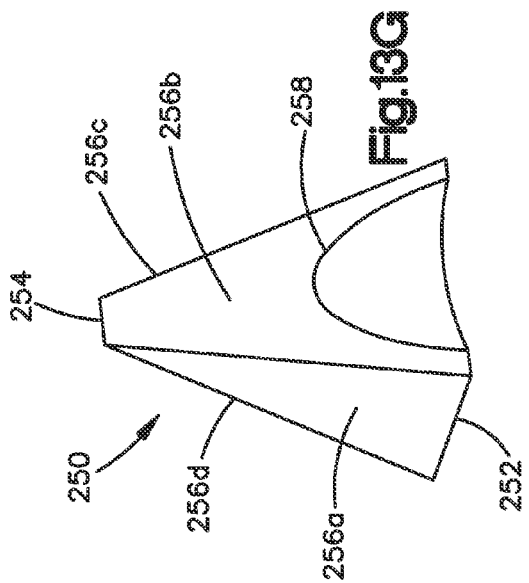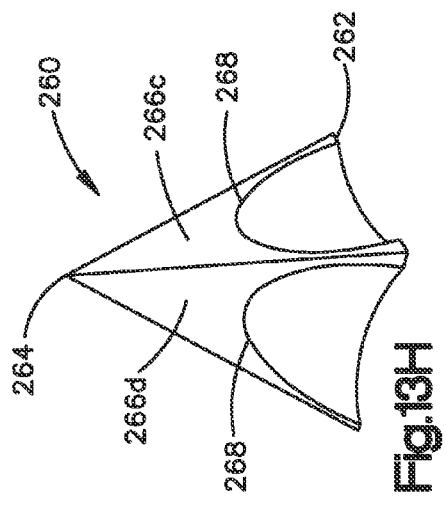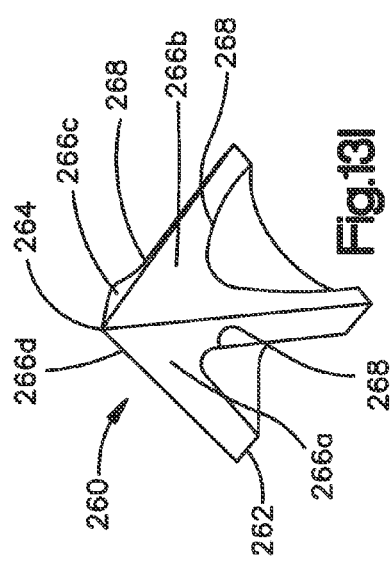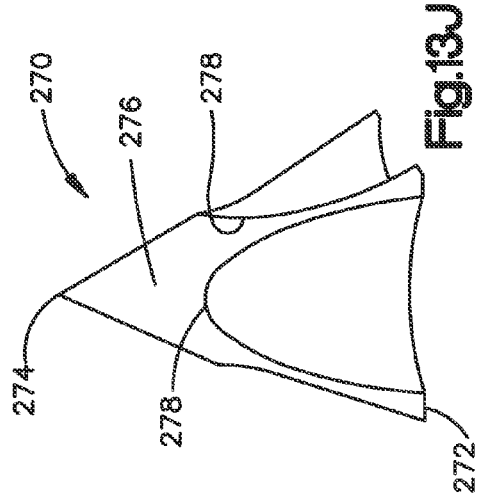

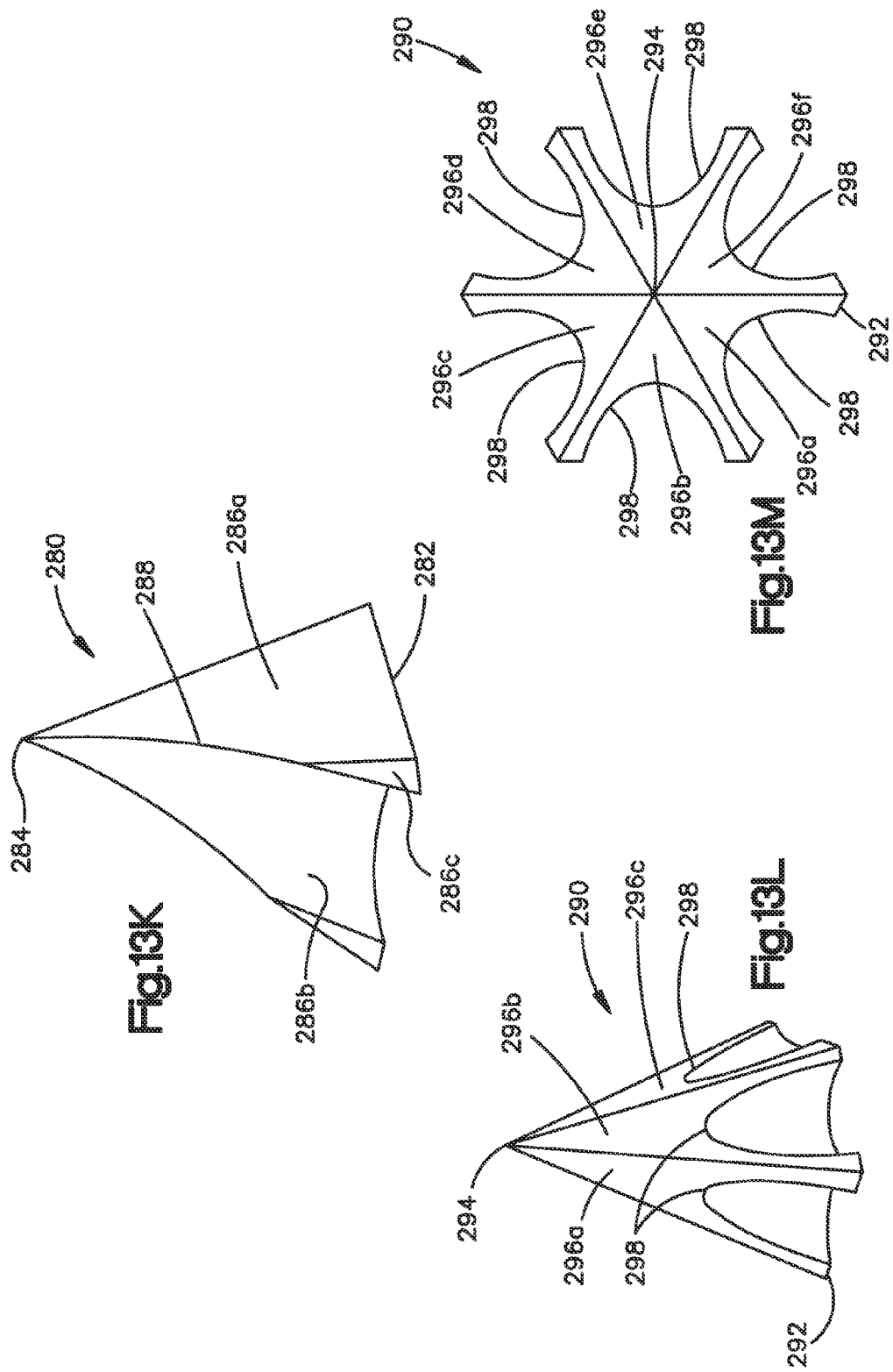

US 8,858,636 B2

INTERVERTEBRAL IMPLANT

BACKGROUND

Historically, complete removal of a disc from between adjacent vertebrae resulted in fusing the adjacent vertebrae together. This "spinal fusion" procedure, which is still in use today, is a widely accepted surgical treatment for symptomatic lumbar and cervical degenerative disc disease. More recently, disc arthoplasty may be utilized to insert an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves and thus the damping effect of the spine. In contrast with fusion techniques, total disc replacement preserves mobility in the motion segment.

One such intervertebral implant includes an upper part mounted to an adjacent vertebra, a lower part mounted to another adjacent vertebra, and an insert located between these two parts. An example of such a total disc replacement intervertebral implant is shown in U.S. Pat. No. 6,936,071, titled "Intervertebral Implant", the contents of which are incorporated herein by reference in their entirety. To provide an anchor to mount the upper and lower parts to the adjacent vertebrae, each part includes a vertically extending keel. While this and other known implants represent improvements in the art of artificial intervertebral implants, there exists a continuing need for improvements of these types of implants.

SUMMARY

In accordance with one embodiment, an endplate of an intervertebral implant includes an outer transverse bone facing surface configured to engage a respective adjacent vertebral surface. The endplate further includes at least one bone fixation spike projecting out from the bone facing surface. The fixation spike defines at least one outer surface extending between a base and a tip. The tip is outwardly spaced from the bone facing surface, and the bone fixation spike defines a recess extending into the outer surface at a location between the tip and the base.

BRIEF DESCRIPTION OF THE DRAWINGS

The foregoing summary, as well as the following detailed description of an example embodiment of the application, will be better understood when read in conjunction with the appended drawings. For the purposes of illustrating the flexible anchoring keel and related instruments of the present application, there is shown in the drawings an example embodiment. It should be understood, however, that the application is not limited to the precise arrangements and instrumentalities shown. In the drawings:

FIG. 1A is a perspective view of a pair of vertebral bodies separated by an intervertebral space;

FIG. 1B is a perspective view of the vertebral bodies illustrated in FIG. 1, and an intervertebral implant inserted into the intervertebral space between the two vertebral bodies;

FIG. 3 is an exploded sectional end elevation view of the intervertebral implant illustrated in FIG. 2 taken along line 3-3;

FIG. 4 is a plan view of an inner transverse surface of the first endplate illustrated in FIG. 2;

FIG. 5A is a perspective view of the inlay of the intervertebral implant illustrated in FIG. 3;

FIG. 5B is a top plan view of the inlay illustrated in FIG. 5A

FIG. 5C is a side elevation view of the inlay illustrated in FIG. 5A;

FIG. 5D is an end elevation view of the inlay illustrated in FIG. 5B;

FIG. 6 is a perspective view of a lower plate of the intervertebral implant illustrated in FIG. 2;

FIG. 8A is a front elevation view of the intervertebral implant illustrated in FIG. 2;

FIG. 8B is a front elevation view of the intervertebral implant similar to FIG. 8A, but showing lateral bending rotation;

FIG. 9A is a top plan view of the lower plate of the intervertebral implant illustrated in FIG. 2;

FIG. 9B is a sectional side elevation view of the intervertebral implant illustrated in FIG. 9A, taken along line 9B-9B;

FIG. 9C is a rear end elevation view of the intervertebral implant illustrated in FIG. 9A;

FIG. 9D is an enlarged top plan view of a region 9D of FIG. 9A, illustrating a first or forward spike of the intervertebral implant;

FIG. 9E is an enlarged top plan view of a region 9E of FIG. 9A, illustrating a second or middle spike of the intervertebral implant;

FIG. 9F is an enlarged top plan view of a region 9F of FIG. 9A, illustrating a third or rear spike of the intervertebral implant;

FIG. 10A is a front perspective view of one of the spikes of the endplate illustrated in FIG. 9A constructed in accordance with one embodiment;

FIG. 10B is a rear end elevation view of one of the spikes of the endplate illustrated in FIG. 9A constructed in accordance with another embodiment;

FIG. 10C is a front elevation view of the spike illustrated in FIG. 10A;

FIG. 10D is a top plan view of one of the spikes of the endplate illustrated in FIG. 9A constructed in accordance with another embodiment;

FIG. 10E is a side elevation view of a spike of the endplate illustrated in FIG. 9A constructed in accordance with another embodiment;

FIG. 11B is a sectional side elevation view of the intervertebral implant illustrated in FIG. 11A, taken along line 11B-11B;

FIG. 11C is a rear end elevation view of the intervertebral implant illustrated in FIG. 11A;

FIG. 11D is an enlarged view of a first or forward spike of the intervertebral implant illustrated in FIG. 11A;

FIG. 11E is an enlarged view of a second or middle spike of the intervertebral implant illustrated in FIG. 11A;

FIG. 11F is an enlarged view of a third or rear spike of the intervertebral implant illustrated in FIG. 11A.

FIG. 13A is a perspective view of an endplate carrying a plurality of bone fixation spikes arranged in accordance with an alternative embodiment;

FIG. 13B is a perspective view of a bone fixation spike constructed in accordance with an alternative embodiment;

FIG. 13C is a top plan view of the bone fixation spike illustrated in FIG. 13B;

FIG. 13D is a perspective view of a bone fixation spike constructed in accordance with an alternative embodiment;

FIG. 13E is a perspective view of a bone fixation spike constructed in accordance with an alternative embodiment;

FIG. 13F is a side elevation view of the bone fixation spike illustrated in FIG. 13E;

FIG. 13G is a perspective view of a bone fixation spike constructed in accordance with an alternative embodiment;

FIG. 13H is a perspective view of a bone fixation spike constructed in accordance with an alternative embodiment;

FIG. 13I is a perspective view of the bone fixation spike illustrated in FIG. 13H;

FIG. 13J is a perspective view of a bone fixation spike constructed in accordance with an alternative embodiment;

FIG. 13K is a perspective view of a bone fixation spike constructed in accordance with an alternative embodiment;

FIG. 13L is a perspective view of a bone fixation spike constructed in accordance with an alternative embodiment;

FIG. 13M is a top plan view of the bone fixation spike illustrated in FIG. 13L.

DETAILED DESCRIPTION

Figure 2:
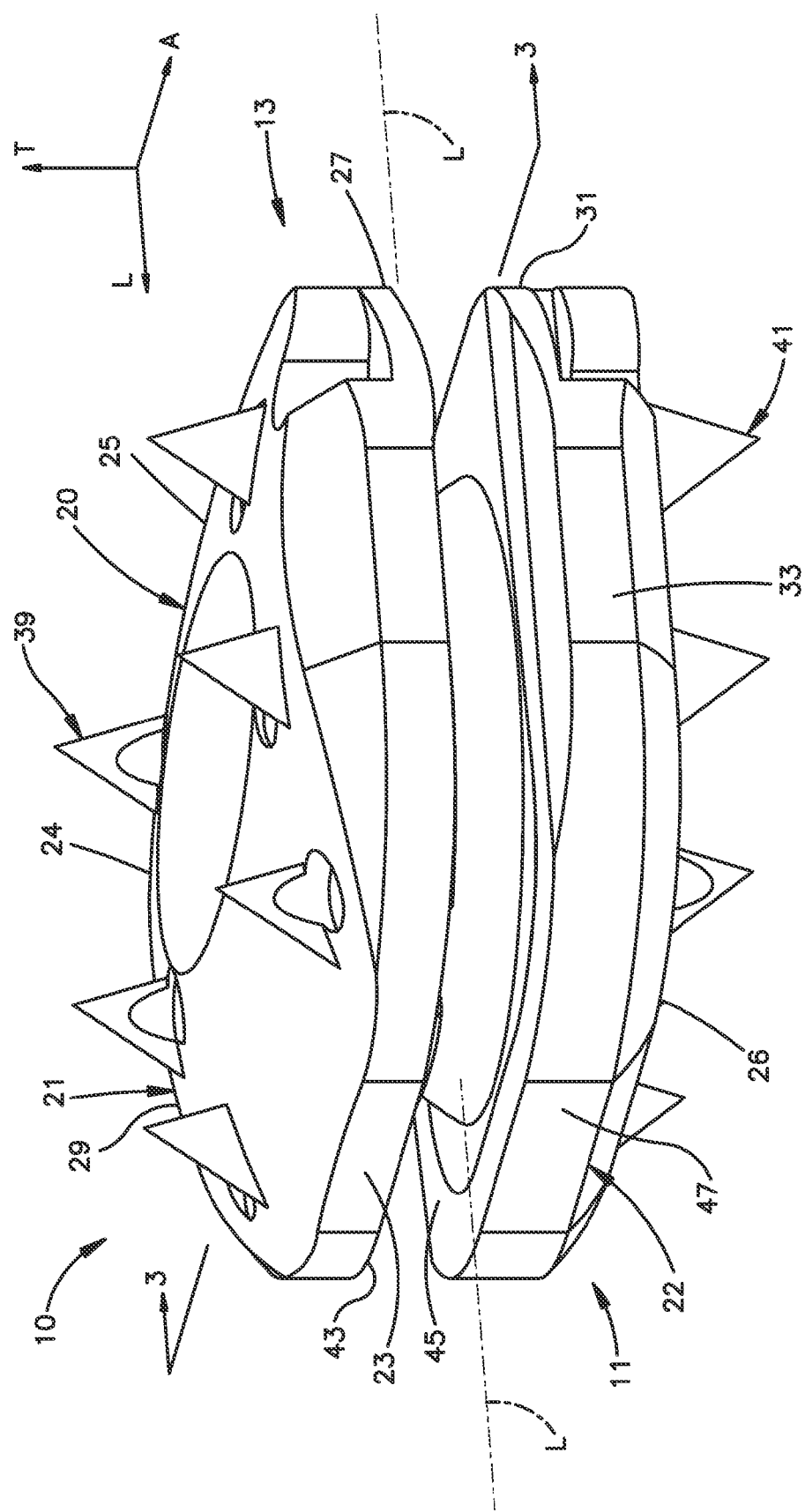
FIG. 2 is a perspective view of an intervertebral implant illustrated in FIG. 1B, constructed in accordance with one embodiment including first and second endplates and an articulation disposed between the endplates.

Referring to FIGS. 1A-B, a superior vertebral body 12a defines a superior vertebral surface 13a of an intervertebral space 14, and an adjacent inferior vertebral body 12b defines an inferior vertebral surface 13b of the intervertebral space 14. Thus, the intervertebral space 14 is disposed between the vertebral bodies 12a-b. The vertebral bodies 12a-b can be anatomically adjacent vertebral bodies, or can remain after a discectomy has been performed that removed a vertebral body from a location between the vertebral bodies 12a-b. As illustrated, the intervertebral space 14 is illustrated after a discectomy, whereby the disc material has been removed to prepare the intervertebral space 14 to receive an orthopedic implant, such as the intervertebral implant 10 illustrated in FIG. 2. Thus, the implant 10 is configured to be inserted into the intervertebral space 14, and achieve restoration of height while maintaining mobility. The intervertebral space 14 can be disposed anywhere along the spine as desired.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases designate preferred positions and orientations in the human body to which reference is made and are not meant to be limiting. The terminology includes the above-listed words, derivatives thereof and words of similar import.

The implant 10 and various components of the implant are described herein extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the implant 10 is implanted into an intervertebral space, such as the intervertebral space 14, the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the implant 10 and its components as illustrated merely for the purposes of clarity and illustration.

Referring now to FIGS. 1-3 generally, the implant 10 generally includes a first or upper component, such as a first or upper endplate 20 adapted to engage the superior vertebral body 12a, and a second or lower component, such as a second or lower endplate 22 adapted to engage the inferior vertebral body 12b. The endplates 20 and 22, and components thereof, can be formed from a variety of biocompatible materials, such as cobalt chromium molybdenum (CoCrMo), titanium and titanium alloys, stainless steel, ceramics, or polymers such as polyetheretherketone (PEEK), polyetherketoneketone (PEKK), bioresorbable materials, and bonegraft (for example allograft and xenograft). A coating may be added or applied to the endplates 20 and 22 to improve physical or chemical properties. The coatings may help to ensure bony in or on growth or medication. Examples of coatings include plasma-sprayed titanium coating or Hydroxyapatite.

The upper endplate 20 includes an upper endplate body 21 that defines a longitudinally front end 23, which provides a leading end with respect to insertion of the implant 10 into the intervertebral disc space 14. The upper endplate body 21 further defines an opposing longitudinally rear end 25, which provides a trailing end with respect to insertion of the implant 10 into the intervertebral disc space 14. The upper endplate body 21 further defines opposing first and second lateral sides 27 and 29, respectively, connected between the front and rear ends 23 and 25, respectively. The upper endplate 20 extends along a central longitudinal axis L-L that divides the body 21 into first and second opposing lateral regions 49A and 49B, respectively (see FIG. 9A). The lateral side 27 defines the lateral boundary of the lateral region 49A, while the lateral side 29 defines the lateral boundary of the lateral region 49B. The upper endplate body 21 further presents an upper, or outer transverse bone facing surface 24, and an opposing lower, or inner transverse surface 43. The upper endplate 20 includes a plurality of bone fixation spikes 39 projecting transversely outward, or up, from the bone facing surface 24 of the upper endplate body 21.

Similarly, the lower endplate 22 includes a lower endplate body 37 that defines a longitudinal front end 47, which provides a leading end with respect to insertion of the implant 10 into the intervertebral disc space 14. The lower endplate body 37 further defines an opposing longitudinal rear end 31, which defines a trailing end with respect to insertion of the implant 10 into the intervertebral disc space 14. The lower endplate body 37 also defines first and second laterally opposed sides 33 and 35, respectively, connected between the front and rear ends 47 and 31, respectively. The lower endplate 22 extends along a central longitudinal axis L-L that divides the body 23 into first and second opposing lateral regions 51A and 51B, respectively (see FIG. 11A). The lateral side 33 defines the lateral boundary of the lateral region 51A, while the lateral side 35 defines the lateral boundary of the lateral region 51B. The lower endplate body 37 further presents a lower, or outer transverse bone facing surface 26, and an opposing upper, or inner transverse surface 45. The lower endplate 22 includes a plurality of bone fixation spikes 41 projecting transversely outward, or down, from the bone facing surface 26.

Figure 11A:
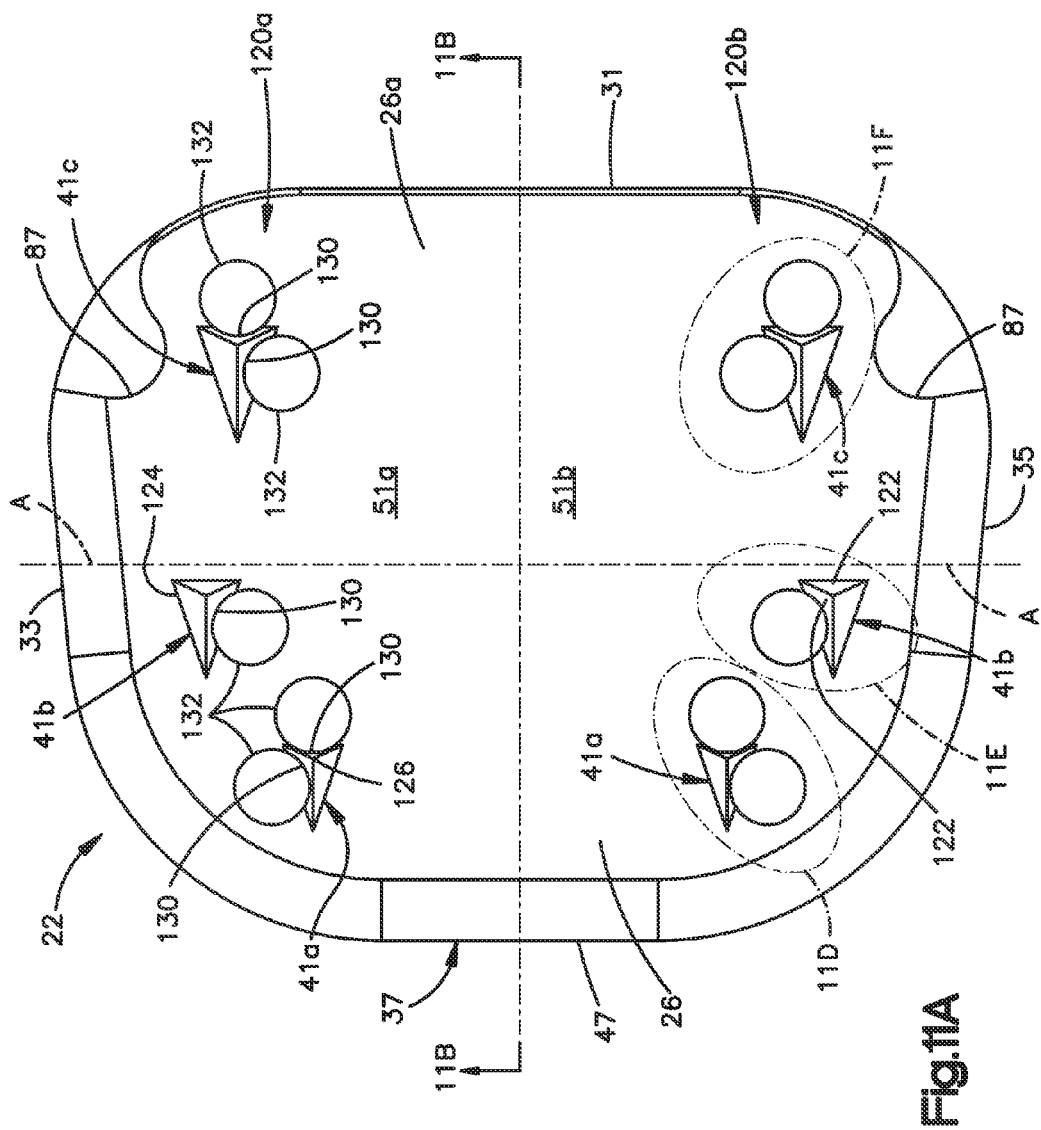
FIG. 11A is a top plan view of the upper plate of the intervertebral implant illustrated in FIG. 2.

The front and rear ends of the endplates 20 and 22 are separated along the longitudinal direction L by a central lateral axis A-A (see FIGS. 9A and 11A). The bone facing surfaces 24 and 26 are separated along a transverse axis T-T that extends in the transverse direction T. In accordance with one embodiment, the front ends 23 and 47 of the endplates 20 and 22 define a posterior end 11 of the implant 10 with respect to the intervertebral space 14, while the rear ends 25 and 31 of the endplates 20 and 22 define an opposing anterior end 13 of the implant 10 with respect to the intervertebral space 14. Otherwise stated, the front or leading ends 23 and 47 of the endplates 20 and 22 are inserted into the posterior region of the intervertebral space 14, while the rear or trailing ends 25 and 31 of the endplates 20 and 22 are inserted into the anterior region of the intervertebral space 14. The implant 10 is configured to be inserted into the intervertebral space 14 along a forward longitudinal direction that extends from the rear end 13 toward the front end 11.

Referring now to FIGS. 3-6, the endplates 20 and 22 each carry complementary first and second joint members 75 and 77, respectively, which each provide rounded mating surfaces and are in operative contact with each other so as to provide an articulating joint 42 that allows the endplates 20 and 22 universal movement relative to each other. The first joint member 75 can be provided as a plastic insert 44 supported by the upper endplate 20, while the second joint member 77 can be provided as a plastic inlay 48 supported by the lower endplate 22. The insert 44 defines a first joint surface 46 or articulation surface, and the plastic inlay 48 defines a second joint surface 50 or articulation surface that interfaces with the first joint surface 46, such that the joint 42 is configured to pivot the endplates 20 and 22 relative to each other universally about 360°. The joint 48 can be constructed generally as described in U.S. Pat. No. 7,204,852, the disclosure of which is hereby incorporated by reference as if set forth in its entirety herein, or in accordance with any suitable alternative embodiment. The joint members 75 and 77 can be made of any suitable material as desired, such as cobalt chromium, and the joint surface 50 can be made of any suitable material as desired, such as polyethylene. The endplates 20 and 22 can be made from any suitable material as desired, such as polyetheretherketone (PEEK), metal, or the like.

As illustrated in FIGS. 3-4, the upper endplate 20 includes a generally circular pocket 52 that extends into the lower surface 43 of the upper endplate body 21. The pocket 52 has a depth that is less than the height of the upper endplate body 21, such that the pocket 52 terminates at a base 53 without extending through the endplate body 21. The pocket 52 has an outer perimeter 57 that is inwardly recessed with respect to the front end 23, the rear end 25, and the lateral sides 27 and 29. The perimeter 57 can be in the shape of a circle, square, rectangle, or any alternative shape as desired. The pocket 52 can further be stepped so as to define a peripheral shoulder 55 that is upwardly spaced with respect to the lower surface 43, and downwardly spaced with respect to the base 53 of the pocket 52.

The insert 44 includes an insert body 54 that defines a first or upper end 56, an opposing second or lower end 58, and at least one side 60 extending between the upper and lower ends 56 and 58 that corresponds in shape with the perimeter 57 of the pocket 52. The insert 44 includes a lip 62 that projects out from the lower end 58 of the side 60. The lip 62 is recessed from the upper end 56 a distance substantially equal to the distance that the shoulder 55 of the pocket 52 is spaced with respect to the lower surface 43.

Accordingly, the insert body 54 is configured to nest within the pocket 52, such that the lip 62 of the insert body 54 is seated against the shoulder 55 of the pocket, and the upper end 56 is seated against the base 53. The insert 44 can be connected to the upper endplate 20 integrally or discretely, for instance using any suitable attachment mechanism, such as an adhesive, or complementary engagement features, e.g., threads, that mate so as to lock the insert body 54 in the pocket 52. The lip 62 has a height greater than that of the shoulder 55 of the pocket 52, such that the lip 62 projects transversely inward, or down, from the lower surface 43 once the insert 44 has been fastened in the pocket 52 of the upper endplate 20.

The insert 44 defines a concavity 64 that projects upwards into the lower end 58 of the insert body 54. The concavity 64 defines the first joint surface 46, which is round as illustrated. The first joint surface 46 defines a middle portion 46a that is recessed with respect to the lower surface 43 of the upper endplate body 21, and an outer portion 46b that projects down from the lower surface 43 of the upper endplate body 21. In accordance with one embodiment, the first joint surface 46 is substantially dome shaped, thereby permitting 360° articulation between the upper and lower plates 20 and 22, respectively. Alternatively, the first joint surface 46 can be rounded in one or more directions, for instance the longitudinal direction L and/or the lateral direction A if selective articulation is desired. Alternatively still, the first joint surface 46 can be non-rounded if it is desired to prevent the upper and lower plates 20 and 22 from articulating. In this regard, it should be appreciated that the upper and lower plates 20 and 22 can articulate with relative to each other, can be fixed with respect to each other, and can be discretely or integrally connected.

Referring now also to FIGS. 5A-D, the inlay 48 includes an inlay body 68 that defines a base 70 having a front end 72, a longitudinally opposing rear end 74, and laterally opposing sides 76 extending between the front and rear ends 72 and 74. The inlay 48 further includes a substantially dome-shaped projection 79 laterally centered on the base 70, and longitudinally displaced closer to the front end 72 than the rear end 74. The projection 79 defines the second joint surface 50, which is round and substantially dome-shaped, as illustrated. The dome-shaped second joint surface 50 is defined by a radius substantially equal to that of the dome-shaped first joint surface 46 of the concavity 64, such that the first and second joint surfaces 46 and 50, when engaged, can ride along each other as the first and second endplates 20 and 22 articulate or pivot relative to each other. The projection 79 has a height greater than the depth of the concavity 64, such that the base 70 is spaced from the lower surface 43 of the upper endplate 20 when the joint surfaces 46 and 50 are engaged. While the second joint surface 50 is dome-shaped as illustrated, it should be appreciated that the second joint surface 50 can assume any shape as desired as described above with respect to the first joint surface 46, such that the shape of the first and second joint surfaces 46 and 50 are complementary.

The inlay body 68 further includes a pair of guide wings 78 that project laterally out from the sides 76, and a snap-in projection 80 in the form of a wedge 82 that projects down from the base 70. The wedge 82 presents a beveled outer surface 84 that extends upward along a longitudinally forward direction, and a transverse stop surface 86 disposed rearward with respect to the beveled outer surface 84. The guide wings 78 and snap-in projection 80 facilitate insertion of the inlay 48 into the lower endplate 22, as will now be described.

In particular, referring also to FIG. 6, the lower endplate 22 includes an outer rim 50 that extends inward from the upper ends of the opposing lateral sides 33 and 35 and the front end 47 of the lower endplate body 37. The lower endplate body 37 thus defines a channel 88 between the upper transverse surface 45, the outer rim 50, and the lateral sides 33 and 35 and front end 47 (see also FIG. 11B). The lower endplate 22 further includes an inwardly projecting snap-in recess 90 disposed proximate to the rear end 31 of the endplate body 37. The recess 90 defines a beveled surface 92 that is angled transversely upward along a longitudinally forward direction. The recess 90 further defines a transverse stop surface 94 disposed rearward of the beveled surface 92. During assembly of the implant 10, the guide wings 78 are inserted into the channel 88, and the inlay 48 is translated forward along the lower endplate body 37 until the snap-in projection 80 of the inlay 48 snap into the snap-in recess 90 of the lower endplate 22, thereby preventing inadvertent removal of the inlay 48. It should be appreciated that the inlay 48 can alternatively be attached to the lower endplate 22, either integrally or discretely in any manner as desired.

Figure 7A:
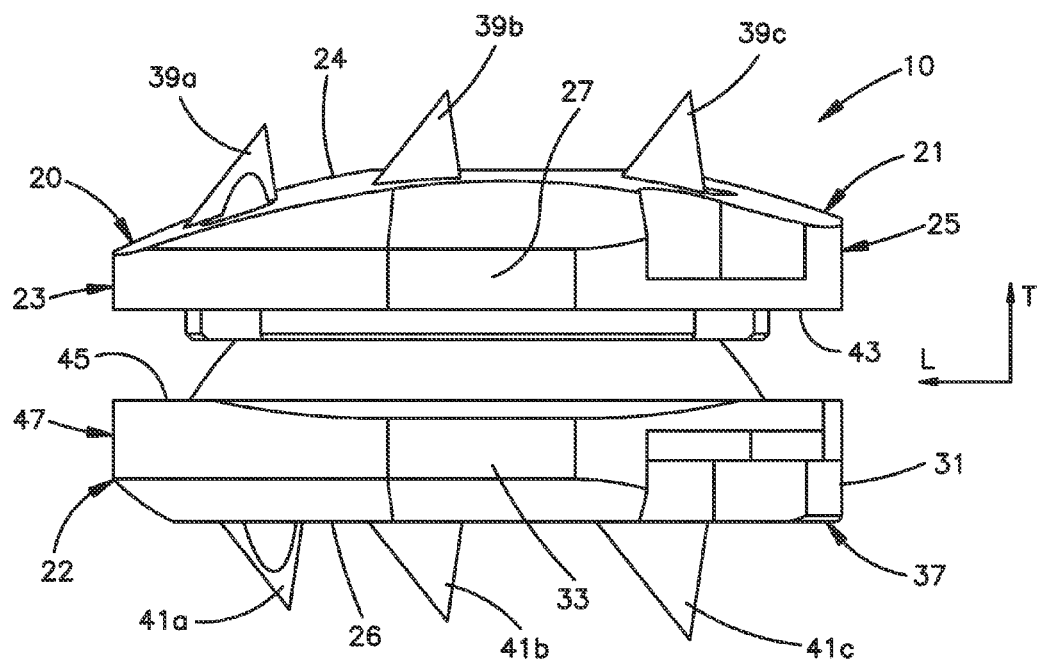
FIG. 7A is a side elevation view of the intervertebral implant illustrated in FIG. 2.
Figure 7B:
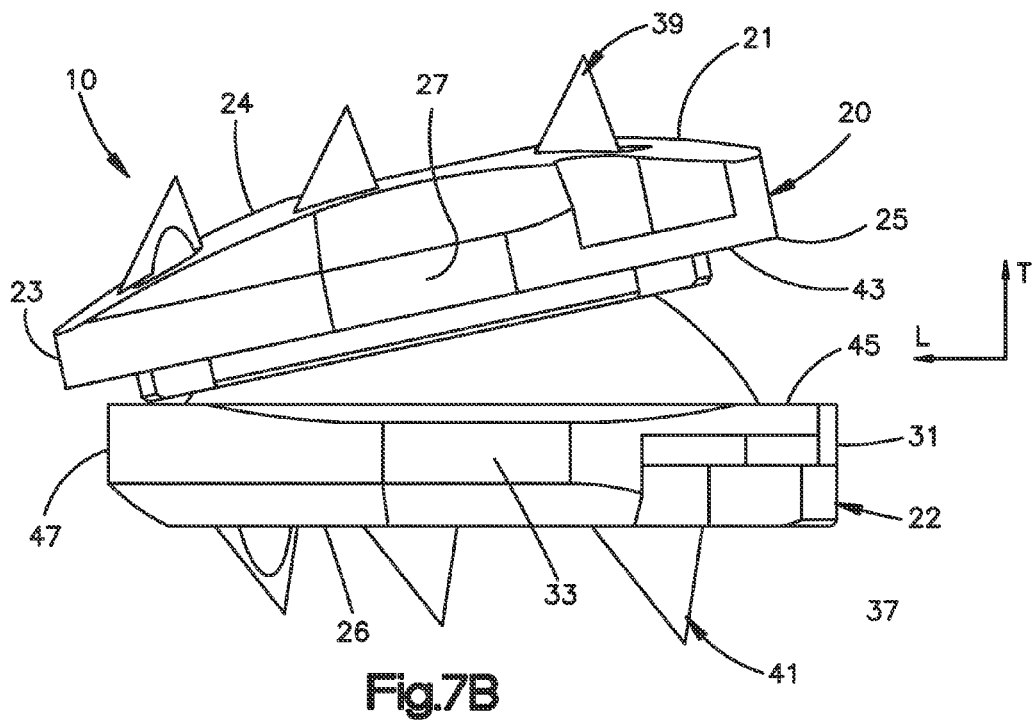
FIG. 7B is a side elevation view of the intervertebral implant similar to FIG. 7A, but showing flexion/extension rotation.

Referring now to FIGS. 7A-B, once the insert 44 of the upper endplate 20 and the inlay 48 of the lower endplate 22 engage, the upper and lower endplates 20 and 22 can pivot relative to each other about a lateral axis, for instance to accommodate flexions and extension of the vertebrae 12a-b. Similarly as illustrated in FIGS. 8A-B, the upper and lower endplates 20 and 22 can pivot relative to each other about a longitudinal axis, for instance to accommodate lateral bending of the vertebrae 12a-b. Alternatively, the pivot axis can lie in any orientation within the horizontal plane defined by the longitudinal and lateral directions. The pivot axis can be coincident with the longitudinal and lateral directions as illustrated in FIGS. 7A-B and FIGS. 8A-B, or the pivot axis can be offset up to 180° with respect to either or both of the longitudinal and lateral directions.

While the joint 42 has been described in accordance with one embodiment, it should be appreciated that the implant 10 could include any alternatively constructed joint (for instance a compliant material such as a silicon cushion joined between the endplates 20 and 22) that enables relative motion between the endplates 20 and 22 in any direction, or that fixedly attaches the endplates 20 and 22. In this regard, it should be appreciated that the upper endplate 20 could carry the second joint member 77 or inlay 48, and the lower endplate 22 could carry the first joint member 75 or insert 44.

The implant 10 can define a width extending along the lateral direction A that can be between approximately 13-20 mm, a length extending along the longitudinal dimension L that can be approximately 10-18 mm, and a height extending between the outer surfaces 24 and 26 along the transverse direction T that can be approximately 4-9 mm. Thus, the implant 10 is suitable for implantation in an intervertebral space in the cervical and upper thoracic regions of the spine, which is characterized by the need for precision because of the relatively small dimensions of cervical intervertebral spaces.

The dimensions described above with respect to the implant 10 in the illustrated embodiment are in contrast to the dimensions of the implant 10 if the implant were to be inserted into an intervertebral space in the a different spinal region, for instance the lumbar or thoracic region. For instance, when the implant 10 is configured for implantation into the lumbar region, the implant can have a width of approximately 25-37 mm, a length of approximately 30-56 mm, and a height of approximately 8-14 mm.

It is to be understood that the implant 10 can be constructed with any dimensions desirable for implantation of any intervertebral space along the spine, and is not limited to the cervical and lumbar regions unless otherwise indicated. Furthermore, while the implant 10 is configured as a total disc replacement device, implants constructed in accordance with the teachings described herein are readily configurable for use with a range of bone-anchored orthopedic prostheses, such as interbody spacers, hip and knee replacement implants, and the like. Furthermore, while the implant 10 has been generally described in accordance with one embodiment, it should be appreciated that the implant 10 can alternatively be constructed in accordance with any embodiment, such that the implant defines an upper, or superior, bone facing surface and an opposing lower, or inferior, bone facing surface. In one alternative embodiment, either or both of the endplates 20 and 22 can include a keel as described in U.S. Pat. No. 7,204,852, the disclosure of which is hereby incorporated by reference as if set forth in its entirety herein.

Referring now to FIGS. 9A-F and 10A-E, the bone facing surface 24 of the upper endplate body 21 includes a longitudinally front section 24a, a longitudinally rear section 24c, and an intermediate section 24b extending longitudinally between the front section 24a and the rear section 24c. Each section 24a-c extends laterally between the first and second lateral sides 27 and 29, which can both be beveled as illustrated. The upper endplate 20 includes laterally opposing notches 85 extending into the rear end 25 of the endplate body 21 that are sized and shaped to receive the distal end of an upper arm of insertion tool configured to insert the implant into an intervertebral space.

The front section 24a extends down, or transversely inward, with respect to a longitudinally forward direction along the bone facing surface 24, and terminates at the front end 23 of the endplate body 21. The rearward section 24c extends down, or transversely inward, with respect to a longitudinally rearward direction along the bone facing surface 24, and terminates at the rear end 25 of the endplate body 21. The front section 24a is longitudinally longer than the rear section 24c, and extends further down than the rear section 24c. The intermediate section 24b extends substantially horizontally between the front section 24a and the rear section 24c. It should be appreciated that the bone facing surface 24 has been described in accordance with the illustrated embodiment, and the surface 24 could assume any alternative shape as desired. For instance, the surface 24 can be substantially planar, or can include at least one non-planar surface, such as the three surfaces 24a-c illustrated and described above.

As described above, the upper endplate 20 includes at least one spike 39, such as a plurality of spikes 39 projecting up from the bone facing surface 24 of the endplate body 21. The spikes 39 are arranged in first and second symmetrical and substantially identically constructed groups 100A and 100B. The first group 100A of spikes 39 is disposed in the lateral region 49A of the endplate body 21, and the second group 100B is disposed in the lateral region 49B of the endplate body 21. Each group 100A-B includes a first or longitudinally forward or front spike 39A, a second or longitudinally middle spike 39B, and a third or longitudinally rear spike 39C, such that the longitudinally middle spike 39B is disposed longitudinally between the forward spike 39A and the rear spike 39C, and forward of the central lateral axis A-A. The spikes 39A-C of the first group 100A can be constructed substantially identically and symmetrically with respect to the spikes 39A-C of the second group 100B.

Each spike 39 can include as many surfaces 102 as desired, such as at least one surface 102, and has substantially pyramidal shape in accordance with the illustrated embodiment. Each spike 39 extends up from a base 104 having a triangular or alternatively shaped footprint at the bone facing surface 24, to an upper or outer transverse tip 106. Each surface 102 extends between the base 104 and the tip 106, and can be connected between the base 104 and the tip 106 as illustrated. The spike 39 thus defines a transverse axis 115 that extends transversely between the outer tip 106 and the bone facing surface 24.

The tips 106 of each spike 39A-C of each group 100A-B can be laterally offset from each other. Accordingly, the spikes 39 can each create their own tracks in the complementary vertebral surface 13a during insertion of the implant 10, and thus engage the bone so as to resist expulsion forces. In accordance with the illustrated embodiment, the tip 106 of the forward spike 39A is disposed laterally inward with respect to the tips 106 of the both the middle spike 39B and the rear spike 39C. The tip 106 of the middle spike 39B is disposed laterally outward with respect to the tips 106 of the both the forward spike 39A and the rear spike 39C. The tip 106 of the rear spike 39C is disposed laterally outward with respect to the tip 106 of the forward spike 39A, and laterally inward with respect to the tip 106 of the middle spike 39B. As illustrated, the tips 106 of the middle spike 39B and the rear spike 39C can be longitudinally spaced from each other a distance greater than the longitudinal distance that the tip 106 of the forward spike 39A and the tip 106 of the middle spike 39B are spaced. For instance, in accordance with one embodiment, the bases 104 of each of the longitudinally spaced spikes 39A-C are longitudinally spaced from each other.

The tip 106 is disposed at a location that is laterally and longitudinally inside the triangular footprint of the base 104. Alternatively, the tip 106 can be disposed on the boundary of the footprint of the base 104, or outside the footprint of the base 104 if desired. Each spike 39 can include three surfaces 102a-c that each extend along an outer transverse directional component, and thus extend out, or up, from the base 104 toward the tip 106. The surfaces 102a-c can be substantially triangular in shape as illustrated, or can alternatively assume any suitable geometric shape as desired. The surfaces 102a-c can extend up from the base 104, and terminate at the tip 106.

Each spike 39 includes a pair of front surfaces 102a and 102b that each extends along a direction having an outer transverse directional component (e.g., extending up from the bone facing surface 24), a longitudinally rearward directional component (e.g., angled longitudinally rearward along an outer transverse direction along the surfaces 102a-b), and a laterally inward directional component (e.g., angled laterally inward along an outer transverse direction along the surfaces 102a-b). Otherwise stated, a line extending up from the base 104 along the surfaces 102a-b will travel longitudinally rearward and laterally inward. In accordance with alternative embodiments, it should be appreciated that the front surfaces 102a-b can extend along a direction that has at least one of the above-mentioned directional components. For instance, it should be appreciated that the surfaces 102a-b could alternatively extend perpendicular with respect to the bone facing surface 24. Each of the surfaces 102a-c extends at an angle with respect to a horizontal plane, defined by the lateral and longitudinal directions, within a range having a lower end greater than 0°, and an upper end less than or equal to 90°.

In accordance with the illustrated embodiment, the front surface 102a of each spike 39 is disposed laterally inward with respect to the front surface 102b. Otherwise stated, the front surface 102a defines a medial surface of the spike 39, while the front surface 102b defines a lateral surface of the spike 39. The front surfaces 102a-b converge laterally along the outer transverse direction from the base 104 to the tip 106. The front surfaces 102a-b further laterally converge along a forward longitudinal direction to a front tip 108. The front surfaces 102a and 102b extend from the base 104 to the outer transverse tip 106, and are joined to each other at their upper ends at a front interface 105. The front interface 105 extends in a substantially longitudinal direction between the front tip 108 and the outer transverse tip 106. The front surfaces 102a-b thus diverge from the front tip 108 along the longitudinally rearward direction, and terminate at a rear surface 102c. It should be appreciated that the spikes 39 are described with respect to their orientation as illustrated, and that the spikes 39 could be alternatively oriented such that the surfaces 102a-c extend in any direction as desired.

The rear surface 102c extends along a direction that has an outer transverse directional component, and a longitudinally forward directional component. Otherwise stated, the rear surface 102c extends transversely out from the bone facing surface 24, and a line extending along the rear surface 102c in the transversely outward direction extends longitudinally forward. In accordance with the illustrated embodiment, the rear surface 102c extends longitudinally forward from the base 104 and terminates at the tip 106. In accordance with alternative embodiments, it should be appreciated that the rear surface 102c can extend along a direction that has at least one of the above-mentioned directional components. For instance, it should be appreciated that the surfaces 102a-b could alternatively extend perpendicular with respect to the bone facing surface 24.

As illustrated, the rear surface 102c extends laterally between the rear ends of the forward surfaces 102a-b, so as to define a first rear interface 107 with respect to the front surface 102a, and a second rear interface 109 with respect to the front surface 102b. The rear interfaces 107 and 109 each extend longitudinally forward from, transversely out from, and laterally in from, the base 104 in a direction toward the tip 106. The interfaces 105, 107, and 109 can extend substantially straight, or can assume any alternative shape, such as curved, as desired. As illustrated in FIG. 10D, the spikes define a distance D extending linearly from the front tip 108 to the inner transverse ends of the rear interfaces 107 and 109 within a range between approximately 1.5 mm and 2.0 mm.

As illustrated in FIG. 9B, the interface 105 defines a first angle $\theta_1$ with respect to the longitudinal axis L-L, and the interfaces 107 and 109 define a second angle $\theta_2$ with respect to the longitudinal axis L-L that is bigger than the first angle $\theta_1$. Alternatively, it should be appreciated that the second angle $\theta_2$ can be less than or equal to the first angle $\theta_1$. The angles can further be different for each spike. As illustrated in FIG. 10E, in accordance with one embodiment, the interface 105 defines an angle $\alpha_1$ between about 0° and about 15° with respect to a transverse axis, and the interface 105 defines an angle $\alpha_2$ between about 30° and about 60° with respect to the interface 107.

The interfaces 105 and 107, in combination with the base 104, define an acute triangle with respect to a view from the longitudinal axis L-L toward the corresponding lateral side, and further respect to a view from the corresponding lateral side toward the longitudinal axis L-L. Alternatively, the interfaces 105 and 107 and the base 104 could define an isosceles triangle, an equilateral triangle, a right triangle, an obtuse triangle, or any alternative geometric shape as desired. Likewise, the interfaces 105 and 109, in combination with the base 104, define an acute triangle with respect to a view from the longitudinal axis L-L toward the corresponding lateral side, and further respect to a view from the corresponding lateral side toward the longitudinal axis L-L. Alternatively, the interfaces 105 and 109 and the base 104 could define an isosceles triangle, an equilateral triangle, a right triangle, an obtuse triangle, or any alternative geometric shape as desired. As illustrated in FIG. 9D-F, the interfaces 107 and 109, in combination with the base 104, define an isosceles triangle, though it should be appreciated that the interfaces 107, 109, and the base 104 could alternatively define an equilateral triangle, a right triangle, an obtuse triangle, or any alternative geometric shape as desired.

Referring now to FIGS. 9A-C, each of the spikes 39A-C defines an absolute height $H_A$ with respect to the bone facing surface 24, and a relative height $H_R$, when the endplate is horizontally oriented, with respect to a common horizontal plane H extending along the lateral and longitudinal directions, such as the inner transverse surface 43, or the inner transverse surface 45 of the lower endplate 22 when the implant is in a horizontally oriented, non-articulated, position. In accordance with the illustrated embodiment, the absolute height $H_A$ can be between 0.5 mm and 4.0 mm, including a range between approximately 1.5 mm and approximately 2.5 mm, such as a range between approximately 1.5 mm and approximately 2.0 mm (see also FIG. 10B). The relative height $H_R$ can be between approximately 1.5 mm and approximately 10 mm, including a range between approximately 2.0 mm and approximately 7.0 mm.

In accordance with the illustrated embodiment, the relative height $H_R$ of at least two of the spikes 39, up to all of the spikes 39, can increase in a longitudinally rearward direction. Otherwise stated, the transverse distance between a common horizontal plane from the respective outer transverse tip 106 of each spike 39 increases along the longitudinally rearward direction. Accordingly, the relative height of the forward spike 39A is less than the relative height of the relative height of the middle spike 39B, which in turn is less than the relative height of the rear spike 39C. The difference in relative height between the forward spike 39A and the middle spike 39B is greater than the difference in relative height between the middle spike 39B and the rear spike 39C in accordance with the illustrated embodiment.

However, because the bone facing surface 24 is non-planar in accordance with the illustrated embodiment, the relationship of the absolute heights of the spikes 39A-C with respect to each other need not be as described with respect to the relative heights of the spikes 39A-C. For instance, because the base 104 of the forward spike 39A is disposed below the base 104 of the middle spike 39B, the absolute height of the forward spike 39A can be greater than the absolute height of the middle spike 39B, such that the relative height of the forward spike 39A is less than the relative height of the middle spike 39B. However, because the base 104 of the rear spike 39C is disposed below the base 104 of the middle spike 39B, the rear spike 39C has an absolute height that is greater than the absolute height of the middle spike 39B, such that the rear spike 39C has a relative height greater than that of the middle spike 39B as described above.

It should be appreciated that the relationship of the absolute heights of the spikes 39A-C with respect to each other can therefore depend on the shape of the bone facing surface 24. For instance, if the bone facing surface 24 is substantially planar, then the absolute height of the forward spike 39A would be less than that of the middle spike 39B, which would be less than that of the rear spike 39C.

With continuing reference to FIGS. 9A-F, at least one up to all of the spikes 39A-C defines a recess 110 extending into at least one of the surfaces 102a-c. For instance, the forward spike 39A defines a recess 110 extending into the laterally outer front surface 102a, while the middle spike 39B and the rear spike 39C each defines a recess 110 extending into the laterally inner front surface 102b and the rear surface 102c. FIG. 10B illustrates a recess 110 extending into the rear surface 102c of a spike 39. FIGS. 10A and 10C illustrate a recess extending into the front surfaces 102a and 102b. FIG. 10D illustrates a recess 110 extending into all surfaces 102a-c. The recess 110 extending into the laterally front surface 102a extends between the front interface 105 and the rear interface 107. Similarly, the recess 110 extending into the laterally inner front surface 102b extends between the front interface 105 and the rear interface 109. The recess 110 extending into the rear surface 102c extends between the rear interfaces 107 and 109.

Thus, in accordance with one embodiment, the recess 110 extends into the respective surface 102 along at least one or both of a lateral directional component and a longitudinal directional component. Furthermore, in accordance with one embodiment, the recess 110 projects inward with respect to a plane defined by at least two outer edges of the surface 102 in which the recess 110 is disposed. Alternatively, the entire surface 102 can be provided in the shape of the recess 110.

Because at least one of the spikes 39 defines a recess 110 in its medial side, and at least one of the spikes 39 defines a recess 110 in its lateral side, movement of the implant 10 is restricted as the spikes 39 penetrate the complementary vertebral surface 13a. It should be appreciated, however, that the spikes 39A-C can alternatively define a recess in one or more, up to all, of the surfaces 102a-c. For instance, the spikes 39 can define a first recess 110 in one of the surfaces 102, and a second recess in another one of the surfaces 102. Alternatively or additionally, a single recess 110 can extend into a pair of adjacent surfaces 102.

The recess 110 is vertically or transversely elongate, and extends up from the base 104 and terminates at a location transversely inward of the tip 106. In accordance with the illustrated embodiment, the recess 110 is shaped as arc in the horizontal plane, that is transversely elongate so as to define a partial cylindrical surface, and is provided in one embodiment as a cut out of the corresponding surface or surfaces 102a-c. For instance, a cylindrical bore 112 can be milled or otherwise formed into, but not through, the endplate 20. The location of the bore 112 can be disposed adjacent a desired surface of the spike 39, such that the milling operation cuts the cylindrically shaped recess 110 into the spike 39. It should be appreciated that the milling operation need not extend into the endplate 20, but could instead terminate once the recess 110 has reached its desired transverse depth, for instance to the base 104 of the spike 39. The depth of the recess 110 into the surface 102 of the spike 39 can thus depend on the alignment between the location of the bore 112 and the surface 102.

As illustrated in FIG. 9B, the recess 110 extending into the inner front surface 102 of the middle spike 39B has a height bigger than the recess 110 extending into the inner front surface 102 of the rear spike 39C, though the height of the recess 110 of the middle spike 39B could be equal to or less than that of the rear spike 39C. Likewise, the height of the recess 110 of the forward spike 39A could be equal to, greater than, or less than, that of the middle spike 39B and rear spike 39C. As illustrated in FIGS. 9D-F, the recesses 110 are arc-shaped in transverse cross section, and extend less than 180° as illustrated, though the arc can alternatively have any length as desired. In accordance with the illustrated embodiment, the arc length of the recesses 110 increases along an inner transverse direction. Of course, it should be appreciated that the arc length of the recesses 110 could alternatively remain substantially constant along an inner transverse direction. Furthermore, it should be appreciated that the recesses 110 can be provided as any shape projecting into the respective surface or surfaces 102 of the spike, for instance a polygonal shape such as triangular, rectangular, hexagonal, octagonal, or an oval or any other shape as desired. It has been found that the recesses 110 reduce the cross-sectional dimension of the spikes 39, and thus are easily penetrable into the complementary vertebral surface 13a.

It should be appreciated that while the spikes 39 have been described in accordance with the illustrated embodiment, the spikes 39 can have any suitable alternative shape as desired. For instance, one or more, up to all of the surfaces 102a-c could be shaped in accordance with any suitable alternative embodiment. It should further be appreciated that the spikes 39 are not intended to be limited to having the three surfaces 102a-c. Rather, in accordance with one embodiment, at least one of the spikes 39 has at least one surface that defines a recess, such as the recess 110 as illustrated and described above.

It should be appreciated that while each group 100A-B includes three spikes 39 as illustrated, each group can include any number of spikes 39, including less than three and more than three, for instance at least one spike 39. In general, higher loads experienced by the implant 10 can justify a greater number of spikes. For instance, each group can include ten or more spikes when the implant 10 is implemented in the lumbar region. The at least one spike 39 can be disposed in any of the front section 24a, the intermediate section 24b, and the rear section 24c.

Furthermore it should be appreciated that the upper endplate 20 includes at least one spike 39 that can be disposed at either the first lateral region 49A, the second lateral region 49B, or coincident with the central longitudinal axis L-L. Furthermore, it should be appreciated that each of the spikes 39 can be constructed in accordance with any of the embodiments as described above with respect to spikes 39A-C. It should also be appreciated that the spikes 39A-C of the first group 100A can be constructed substantially identically with respect to the corresponding spikes 39A-C of the second group 100B as illustrated, or alternatively the spikes 39A-C of the first group 100A can be constructed differently than the corresponding spikes 39A-C of the second group 100B.

Referring now to FIGS. 11A-F, the bone facing surface 26 of the lower endplate body 37 is beveled at its front end 47, and includes a substantially planar horizontal surface 26a that extends generally parallel with the inner surface 45. The horizontal surface 26a extends laterally between the first and second lateral sides 33 and 35, which can both be beveled as illustrated. The lower endplate 22 includes laterally opposing notches 87 extending into the rear end 31 of the endplate body 37 that are sized and shaped to receive the distal end of a lower arm of insertion tool configured to insert the implant 10 into an intervertebral space. It should be appreciated that the bone facing surface 26 has been described in accordance with the illustrated embodiment, and the surface 26 could assume any alternative shape as desired. For instance, the surface 26 can be constructed substantially as described with respect to the bone facing surface 24 of the upper endplate 20, or in accordance with any desired alternative embodiment.

As described above, the lower endplate 22 includes at least one spike 41, such as a plurality of spikes 41 projecting down from the bone facing surface 26 of the endplate body 37. In accordance with the illustrated embodiment, the spikes 41 project down from the planar surface 26a. The spikes 41 are arranged in first and second symmetrical and substantially identically constructed groups 120A and 120B. The first group 120A of spikes 41 is disposed in the lateral region 51A of the endplate body 37, and the second group 120B is disposed in the lateral region 51B of the endplate body 37. Each group 120A-B includes a longitudinally forward or front spike 41A, a longitudinally rear spike 41C, and a longitudinally middle spike 41B disposed longitudinally between the forward spike 41A and the rear spike 41C, and forward of the central lateral axis A-A. The spikes 41A-C of the first group 120A can be constructed substantially identically and symmetrically with respect to the spikes 41A-C of the second group 120B.

Each spike 41 can include as many surfaces 122 as desired, such as at least one surface 122, and has substantially pyramidal shape in accordance with the illustrated embodiment. Each spike 41 extends up from a base 124 having a triangular or alternatively shaped footprint at the bone facing surface 26, to an upper or outer transverse, tip 126. Each surface 122 extends between the base 124 and the tip 126, and can be connected between the base 124 and the tip 126 as illustrated. The spike 41 thus defines a transverse axis 135 that extends transversely between the outer tip 126 and the bone facing surface 26.

The tips 126 of each spike 41A-C of each group 120A-B can be laterally offset from each other. Accordingly, the spikes 41 can each create their own tracks in the complementary vertebral surface 13a during insertion of the implant 10, and thus engage the bone so as to resist expulsion forces. In accordance with the illustrated embodiment, the tip 126 of the forward spike 41A is disposed laterally inward with respect to the tips 126 of the both the middle spike 41B and the rear spike 41C. The tip 126 of the middle spike 39B is disposed laterally outward with respect to the tips 126 of the both the forward spike 41A and the rear spike 41C. The tip 126 of the rear spike 41C is disposed laterally outward with respect to the tip 126 of the forward spike 41A, and laterally inward with respect to the tip 126 of the middle spike 41B. As illustrated, the tips 126 of the middle spike 419B and the rear spike 41C can be longitudinally spaced from each other a distance greater than the longitudinal distance that the tip 126 of the forward spike 41A and the tip 126 of the middle spike 41B are spaced. For instance, in accordance with one embodiment, the bases 124 of each of the longitudinally spaced spikes 41A-C are longitudinally spaced from each other.

The tip 126 is disposed at a location that is laterally and longitudinally inside the triangular footprint of the base 124. Alternatively, the tip 126 can be disposed on the boundary of the footprint of the base 124, or outside the footprint of the base 124 if desired. Each spike 41 can include any number of surfaces as desired, such as the three surfaces 122*a-c* illustrated, that each extend along an outer transverse directional component, and thus extend out, or down, from the base 124 toward the tip 126. The surfaces 122*a-c* can be substantially triangular in shape as illustrated, or can alternatively assume any suitable geometric shape as desired. The surfaces 122*a-c* can extend down from the base 124, and terminate at the tip 126.

Each spike 41 includes a pair of front surfaces 122*a* and 122*b* that each extends along a direction having an outer transverse directional component (e.g., extending down from the bone facing surface 26), a longitudinally rearward directional component (e.g., angled longitudinally rearward along an outer transverse direction along the surfaces 122*a-b*), and a laterally inward directional component (e.g., angled laterally inward along an outer transverse direction along the surfaces 122*a-b*). Otherwise stated, a line extending down from the base 124 along the surfaces 122*a-b* will travel longitudinally rearward and laterally inward. In accordance with alternative embodiments, it should be appreciated that the front surfaces 122*a-b* can extend along a direction that has at least one of the above-mentioned directional components. For instance, it should be appreciated that the surfaces 122*a-b* could alternatively extend perpendicular with respect to the bone facing surface 26.

In accordance with the illustrated embodiment, the front surface 122*a* of each spike 41 is disposed laterally inward from the front surface 122*b*. Otherwise stated, the front surface 122*a* defines a medial surface of the spike 41, while the front surface 122*b* defines a lateral surface of the spike 41. The front surfaces 122*a-b* converge laterally along the outer transverse direction from the base 124 to the tip 126. The front surfaces 122*a-b* further laterally converge along a forward longitudinal direction to a front tip 128. The front surfaces 122*a* and 122*b* extend from the base 124 to the outer transverse tip 126, and are joined to each other at their upper ends at a front interface 125. The front interface 125 extends in a substantially longitudinal direction between the front tip 128 and the outer transverse tip 126. The front surfaces 122*a-b* thus diverge from the front tip 128 along the longitudinally rearward direction, and terminate at a rear surface 122*c*. It should be appreciated that the spikes 41 are described with respect to their orientation as illustrated, and that the spikes 41 could be alternatively oriented such that the surfaces 122*a-c* extend in any direction as desired.

The rear surface 122*c* extends along a direction that has an outer transverse directional component, and a longitudinally forward directional component. Otherwise stated, the rear surface 122*c* extends transversely out from the bone facing surface 26, and a line extending along the rear surface 122*c* in the transversely outward direction extends longitudinally forward. In accordance with the illustrated embodiment, the rear surface 122*c* extends longitudinally forward from the base 124 and terminates at the tip 126. In accordance with alternative embodiments, it should be appreciated that the rear surface 122*c* can extend along a direction that has at least one of the above-mentioned directional components. For instance, it should be appreciated that the surfaces 122*a-b* could alternatively extend perpendicular with respect to the bone facing surface 26. Each of the surfaces 122*a-c* extends at an angle, with respect to a horizontal plane defined by the lateral and longitudinal directions, within a range having a lower end greater than 0°, and an upper end less than or equal to 90°.

Figure 12A:
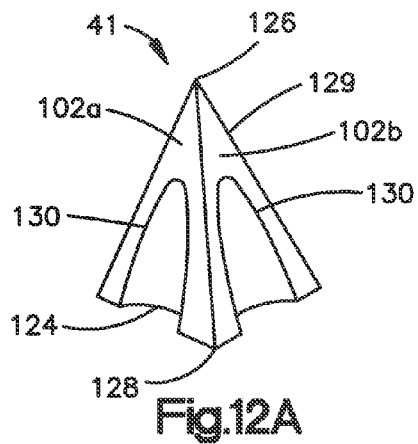
FIG. 12A is a front perspective view of one of the spikes of the endplate illustrated in FIG. 11A constructed in accordance with one embodiment.
Figure 12B:
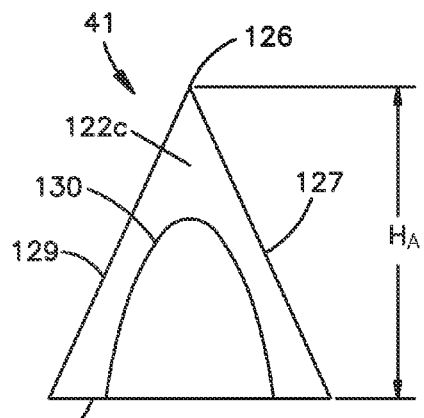
FIG. 12B is a rear end elevation view of one of the spikes of the endplate illustrated in FIG. 1A constructed in accordance with another embodiment.
Figure 12C:
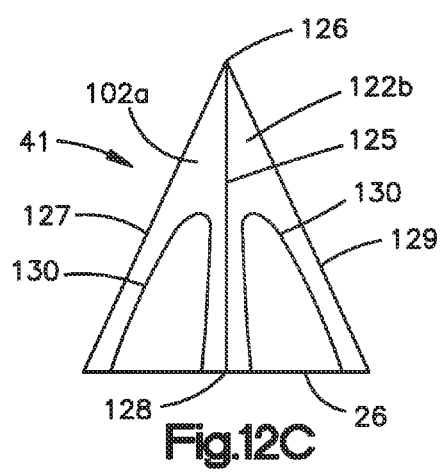
FIG. 12C is a front elevation view of the spike illustrated in FIG. 12A.
Figure 12D:
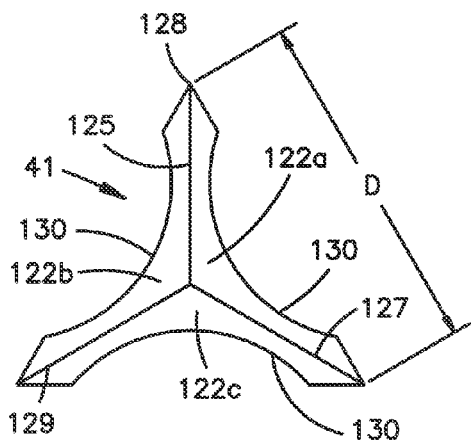
FIG. 12D is a top plan view of one of the spikes of the endplate illustrated in FIG. 11A constructed in accordance with another embodiment.

As illustrated, the rear surface 122*c* extends laterally between the rear ends of the forward surfaces 122*a-b*, so as to define a first rear interface 127 with respect to the front surface 122*a*, and a second rear interface 129 with respect to the front surface 122*b*. The rear interfaces 127 and 129 each extend longitudinally forward from, transversely out from, and laterally in from, the base 124 in a direction toward the tip 126. The interfaces 125, 127, and 129 can extend substantially straight, or can assume any alternative shape, such as curved, as desired. As illustrated in FIG. 12D, the spikes define a distance D extending linearly from the front tip 128 to the inner transverse ends of the rear interfaces 127 and 129 within a range between approximately 1.5 mm and 2.0 mm.

Figure 12E:
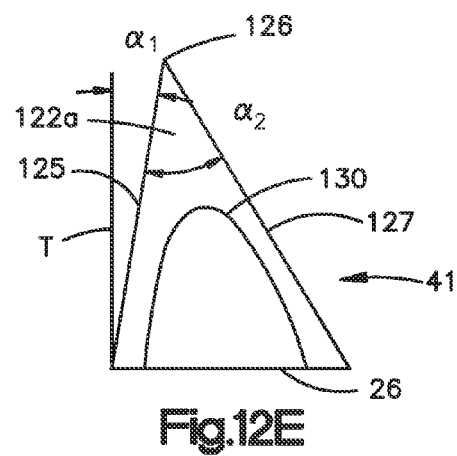
FIG. 12E is a side elevation view of a spike of the endplate illustrated in FIG. 11A constructed in accordance with another embodiment.

Referring also to FIG. 12E, the interface 125 defines a first angle $\alpha 1$ with respect to the longitudinal axis L-L, and the interfaces 127 and 129 define a second angle $\alpha 2$ with respect to the longitudinal axis L-L that is greater than the first angle $\alpha 1$. Alternatively, it should be appreciated that the second angle $\alpha 2$ can be less than or equal to the first angle $\alpha 1$. In accordance with one embodiment, as illustrated in FIG. 12E, the interface 127 defines an angle $\alpha 1$ between about 0° and about 15° with respect to a transverse axis, and the interface 125 defines an angle $\alpha 2$ between about 30° and about 60° with respect to the interface 127.

The interfaces 125 and 127, in combination with the base 124, define an acute triangle with respect to a view from the longitudinal axis L-L toward the corresponding lateral side, and further respect to a view from the corresponding lateral side toward the longitudinal axis L-L. Alternatively, the interfaces 125 and 127 and the base 124 could define an isosceles triangle, an equilateral triangle, a right triangle, an obtuse triangle, or any alternative geometric shape as desired. Likewise, the interfaces 125 and 129, in combination with the base 124, define an acute triangle with respect to a view from the longitudinal axis L-L toward the corresponding lateral side, and further respect to a view from the corresponding lateral side toward the longitudinal axis L-L. Alternatively, the interfaces 125 and 109 and the base 124 could define an isosceles triangle, an equilateral triangle, a right triangle, an obtuse triangle, or any alternative geometric shape as desired. As illustrated in FIG. 11C, the interfaces 127 and 129, in combination with the base 124, define an isosceles triangle, though it should be appreciated that the interfaces 127, 129, and the base 124 could alternatively define an equilateral triangle, a right triangle, an obtuse triangle, or any alternative geometric shape as desired.

Referring now to FIGS. 11A-C, each of the spikes 41A-C defines an absolute height $H_A$ with respect to the bone facing surface 26, and a relative height $H_R$, when the endplate is horizontally oriented, with respect to a common horizontal plane H extending along the lateral and longitudinal directions, such as the inner transverse surface 45, or the inner transverse surface 43 of the upper endplate 20 when the implant 10 is in a horizontally oriented, non-articulated, position. In accordance with the illustrated embodiment, the absolute height $H_A$ can be between 0.5 mm and 4.0 mm, including a range between approximately 1.5 mm and approximately 2.5 mm, for instance a range between approximately 1.5 mm and approximately 2.0 mm (see also FIG. 12B). The relative height $H_R$ can be between approximately 1.5 mm and approximately 10 mm, including a range between approximately 2.0 mm and approximately 7.0 mm.

In accordance with the illustrated embodiment, the relative height $H_R$ of at least two of the spikes 41, up to all of the spikes 41, can increase in a longitudinally rearward direction. Otherwise stated, the transverse distance between a common horizontal plane from the respective outer transverse tip 126 of each spike 41 increases along the longitudinally rearward direction. Accordingly, the relative height of the forward spike 41A is less than the relative height of the relative height of the middle spike 41B, which in turn is less than the relative height of the rear spike 41C. Because the portion 26a of the bone facing surface 26 that supports the spikes 41 is substantially planar and horizontal in accordance with the illustrated embodiment, the relationship of the absolute heights $H_A$ of the spikes 41A-C with respect to each other is as described with respect to the relative heights $H_R$ of the spikes 41A-C.

With continuing reference to FIGS. 11A-F, at least one, and up to all of the spikes 41A-C defines a recess 130 extending into at least one of the surfaces 122a-c. For instance, the forward spike 41A defines a recess 130 extending into the laterally outer front surface 122a and further defines a recess 130 extending into the rear surface 122c. The middle spike 41B defines a recess 130 extending into the laterally inner front surface 102b. The rear spike 41C defines a recess 130 extending into the laterally inner front surface 122b and the rear surface 122c. FIG. 12B illustrates a recess 130 extending into the rear surface 122c of a spike 41. FIGS. 12A and 12C illustrate a recess 130 extending into each of the front surfaces 122a and 122b. FIG. 12D illustrates a recess 130 extending into all surfaces 122a-c. The recess 130 extending into the laterally front surface 122a extends between the front interface 125 and the rear interface 127. Similarly, the recess 130 extending into the laterally inner front surface 122b extends between the front interface 125 and the rear interface 129. The recess extending into the rear surface 122c extends between the rear interfaces 127 and 129.

Thus, in accordance with one embodiment, the recess 130 extends into the respective surface 122 along at least one or both of a lateral directional component and a longitudinal directional component. Furthermore, in accordance with one embodiment, the recess 130 projects inward with respect to a plane defined by at least two outer edges of the surface 122 in which the recess 130 is disposed. Alternatively, the entire surface 122 can be provided in the shape of the recess 130.

Because at least one of the spikes 41 defines a recess 130 in its medial side, and at least one of the spikes 41 defines a recess 130 in its lateral side, movement of the implant 10 is restricted as the spikes 41 penetrate the complementary vertebral surface 13b. It should be appreciated, however, that the spikes 41A-C can alternatively define a recess in one or more, up to all, of the surfaces 122a-c. For instance, the spikes 41 can define a first recess 130 in one of the surfaces 122, and a second recess 130 in another one of the surfaces 122. Alternatively or additionally, a single recess 130 can extend into a pair of adjacent surfaces 122.

The recess 130 is vertically or transversely elongate, and extends up from the base 124 and terminates at a location transversely inward of the tip 126. In accordance with the illustrated embodiment, the recess 130 is shaped as an arc in the horizontal plane, that is transversely elongate so as to define a partial cylindrical surface, and can be provided as a cut out of the corresponding surface or surfaces 122a-c. For instance, a cylindrical bore 132 can be milled or otherwise formed into the bone facing surface 26. The location of the bore 132 can be disposed adjacent a desired surface of the spike 41, such that the milling operation cuts the cylindrically shaped recess 130 into the spike 41. It should be appreciated that the milling operation need not extend into the endplate 26, but could instead terminate once the recess 130 has reached its desired transverse depth, for instance to the base 124 of the spike 41. The depth of the recess 130 into the surface 122 of the spike 41 can thus depend on the alignment between the location of the bore 132 and the surface 122.

As illustrated in FIG. 11B, the recess 130 extending into the laterally inner front surface 122a of the rear spike 41C has a height greater than the recess 130 extending into the laterally inner front surface 122a of the middle spike 41B, though the height of the recess 110 of the rear spike 41C could be equal to or less than that of the middle spike 41C. Likewise, the height of the recess 130 extending into the outer front surface 122b of the forward spike 41A could be equal to, greater than, or less than, that of the recess 130 that extends into the inner front surface 122a of the middle spike 41B and rear spike 41C. As illustrated in FIGS. 11D-F, the recesses 130 are arc-shaped in transverse cross section, and extend less than 180° as illustrated, though the arc can alternatively have any length as desired. In accordance with the illustrated embodiment, the arc length of the recesses 130 increases along an inner transverse direction. Of course, it should be appreciated that the arc length of the recesses 130 could alternatively remain substantially constant along an inner transverse direction. Furthermore, it should be appreciated that the recesses 130 can be provided as any shape projecting into the respective surface or surfaces 122 of the spike 41, for instance a polygonal shape such as triangular, rectangular, oval or any other shape as desired. It has been found that the recesses 130 reduce the cross-sectional dimension of the spikes 41, and thus are easily penetrable into the complementary vertebral surface 13b.

It should be appreciated that while the spikes 41 have been described in accordance with the illustrated embodiment, the spikes 41 can have any suitable alternative shape as desired. For instance, one or more, up to all of the surfaces 122a-c could be shaped in accordance with any suitable alternative embodiment. It should further be appreciated that the spikes 41 are not intended to be limited to having the three surfaces 122a-c. Rather, in accordance with one embodiment, at least one of the spikes 41 has at least one surface that defines a recess, such as the recess 120 as illustrated and described above.

It should be appreciated that while each group 120A-B includes three spikes 41 as illustrated, each group can include any number of spikes 41, including less than three and more than three, for instance at least one spike 41. It has been found that six spikes 41 projecting from the bone facing surface 26 provides adequate penetration into the complementary vertebral surface 13b, while also providing adequately robust fixation. The at least one spike 41 can be disposed at any location on the planar portion 26a of the bone facing surface 26, or elsewhere on the bone facing surface 26.

Furthermore it should be appreciated that the lower endplate 22 includes at least one spike 41 that can be disposed at either the first lateral region 51A, the second lateral region 51B, or coincident with the central longitudinal axis L-L. Furthermore, it should be appreciated that each of the spikes 41 can be constructed in accordance with any of the embodiments as described above with respect to spikes 41A-C. It should also be appreciated that the spikes 41A-C of the first group 120A can be constructed substantially identically with respect to the corresponding spikes 41A-C of the second group 120B as illustrated, or alternatively the spikes 41A-C of the first group 120A can be constructed differently than the corresponding spikes 41A-C of the second group 120B.

The endplates 20 and 22 and various respective bone fixation spikes 39 and 41 that project transversely out from the endplate 20 and 22 have been described in accordance with certain embodiments. However, as described above, the endplates 20 and 22, along with the bone fixation spikes 39 and 41 can be constructed in accordance with numerous alternative embodiments. For instance, the spikes 39 and 41 can be arranged on their respective endplates as illustrated in FIG. 13A. Furthermore, at least one or more, up to all, of the spikes 39 and 41 can be constructed in accordance with any of the embodiments illustrated below in FIGS. 13B-N, or alternatively can include at least one or more up to all of the features or structures described below with respect to the spikes illustrated in at least one or more up to all of FIGS. 13B-N. It should be appreciated that the various structure illustrated in FIGS. 13B-N can be orientated in any direction as desired, such as a longitudinally forward direction, a longitudinally rearward direction, a laterally inward direction, a laterally outward direction, or anywhere between these directions.

Referring now to FIG. 13A, an endplate 200 is illustrated, and can be constructed as described with respect to endplates 20 or 22. Thus, the endplate 200 defines a longitudinally front end 202, an opposing longitudinally rear end 204, and a pair of laterally opposing sides 206. A central longitudinal axis L-L divides the endplate 200 into opposing lateral sections 208a and 208b. The endplate 200 carries three groups 210a-c of bone fixation spikes 212. The groups 210a-c of spikes 212 can be arranged on the endplate 200 as described above with respect to the groups 100A-B and 120A-B. However, FIG. 13A illustrates that more than two groups of spikes 212 can be carried by an endplate, though it should be appreciated that just one group can be carried by an endplate. In accordance with the illustrated embodiment, the first two groups 210a-b are disposed in the lateral sections 208a-b, respectively, while the third group 210c is arranged on the longitudinal axis L-L. Thus, the spikes 212 of one or more, up to all, of the groups can be in partial or total longitudinal alignment. It should be appreciated that FIG. 13A illustrates that the endplate 200 can carry more than six spikes, and more than two groups of spikes. For instance, an endplate can carry any number of laterally offset groups of spikes, for instance one, two, three, four, five, or six groups or more. Each group can include at least one spike, including two, three, four, five, six, seven, eight, nine, ten, or more.

Referring now to FIGS. 13B-C, a bone fixation spike 220 is illustrated as including a base 222 and a tip 224 that is transversely spaced from the bone facing surface of the corresponding endplate in the manner described above. The bone fixation spike 220 includes four outer surfaces 226a-d that extend between the base 222 and the tip 224, and are connected to each other at a 90° angle as illustrated. The outer surfaces 226a-d all have the same horizontal length, such that the spike 220 is in the shape of a square in top plan view as illustrated in FIG. 13C, though the spike 220 could alternatively be rectangular, a parallelogram, quadrilateral, or other four-sided polygon as desired. A recess 228 extends into at least one of the surfaces 226a-d, and extends into all of the surfaces 226a-d in the manner described above with respect to recesses 110 and 130. The recesses 228 can be cylindrical, conical, triangular (having a pointed or rounded apex), or polygonal, for instance including five polygonal surfaces of a pentagon as illustrated. Furthermore, the recesses 228 can be angulated with respect to each other.

Referring now to FIG. 13D, a bone fixation spike 230 is illustrated as including a base 232 and a tip 234 that is transversely spaced from the bone facing surface 235 of a corresponding endplate in the manner described above. The bone fixation spike 230 includes a plurality of outer surfaces, including outer surfaces 236a-c that extend between the base 232 and the tip 234. The outer surfaces 236a and 236c each join opposing edges of the outer surface 236b, so as to define respective interfaces 238a and 238b. The interface 238a extends from the base 232 at an angle $\lambda_1$ which can be approximately 90°, while the interface 238b extends from the bone facing surface 235 at an angle $\lambda_2$ greater than 90°, such as between approximately 90° and 120°. The outer surfaces 236a and 236c further define opposing edges 239a and 239b that are connected between the base 232 and the tip 234 (e.g., extend from the base 232 and the tip 234). Thus, the bone fixation spike 230 illustrates that a bone fixation spike can include one or more edges that extend perpendicular to the base, or the underlying bone facing surface of the corresponding endplate. The bone fixation spike 230 further illustrates that one or more of the outer surfaces can be connected between the tip and the base, while one or more other outer surfaces can extend between the tip and the base without being connected between the tip and the base. A recess of the type described above can extend into one or more, up to all, of these outer surfaces.

Referring now to FIGS. 13E-F, a bone fixation spike 240 is illustrated as including a base 242 and a tip 244 that is transversely spaced from the bone facing surface of the corresponding endplate in the manner described above. The bone fixation spike 240 includes four outer surfaces 246a-d that extend between the base 242 and the tip 244. A first pair of laterally opposing outer surfaces 246a and 246c are triangular, while a second pair of longitudinally opposing outer surfaces 246b and 246d are rectangular. The rectangular outer surfaces 246b and 246d converge toward each other in an outer transverse direction toward the tip 244, and are joined at the tip 244. Thus, the tip is elongate in a direction between the outer transverse apexes of the triangular outer surfaces 246a and 246c. The triangular surfaces 246a and 246c can extend perpendicular from the underlying bone facing surface. A recess 248 can extend into any or all of the surfaces 246a-d, and extends into the surfaces 246b and 246d as illustrated.

Referring now to FIG. 13G, a bone fixation spike 250 is illustrated as including a base 252 and a tip 254 that is transversely spaced from the bone facing surface of the corresponding endplate in the manner described above. The bone fixation spike 250 includes four outer surfaces 256a-d that extend between the base 252 and the tip 254. A first pair of laterally opposing outer surfaces 256a and 256c are triangular, while a second pair of longitudinally opposing outer surfaces 256b and 256d are quadrilaterals, shaped as trapezoids, and in particular isosceles trapezoids. The trapezoidal outer surfaces 256b and 256d converge toward each other in an outer transverse direction toward the tip 254, and are joined at the tip 254. The triangular surfaces 256a and 256c also converge toward each other in an outer transverse direction, however the outer transverse ends of the triangular surfaces 256a and 256c are spaced from each other, such that the tip 254 is elongate between the outer transverse ends. A recess 258 can extend into any or all of the surfaces 256a-d, and extends into the surfaces 256b and 256d as illustrated.

Referring now to FIGS. 13H-I, a bone fixation spike 260 is illustrated as including a base 262 and a tip 264 that is transversely spaced from the bone facing surface of the corresponding endplate in the manner described above. The bone fixation spike 260 includes four outer surfaces 266a-d that extend between the base 262 and the tip 264. Each of the surfaces 266a-d is triangular in shape, and in particular defines an isosceles triangle. The triangular outer surfaces 266a-d converge toward each other in an outer transverse direction toward the tip 264, and are all joined at the tip 264. A recess 268 can extend into any or all of the surfaces 266a-d, and extends into all of the surfaces 266a-d as illustrated.

Referring now to FIG. 13J, a bone fixation spike 270 is illustrated as including a base 272 and a tip 274 that is transversely spaced from the bone facing surface of the corresponding endplate in the manner described above. As described above with respect to spike 39 and 41, it is recognized that spikes extending from an underlying bone facing surface can include at least one outer surface. The bone fixation spike 270 includes one outer surface 276 that has the shape of a cone. One or more recesses 278, for instance between one and eight recesses 278, can extend into the outer surface 276 as desired, and can be circumferentially equidistantly or irregularly spaced about the outer surface 276. In accordance with the illustrated embodiment, the recesses 278 can be 90° circumferentially offset about the conical outer surface 276.

Referring now to FIG. 13K, a bone fixation spike 280 is illustrated as including a base 282 and a tip 284 that is transversely spaced from the bone facing surface of the corresponding endplate in the manner described above. The bone fixation spike 280 includes a plurality of outer surfaces, such as outer surfaces 286a-c that extend between the base 262 and the tip 264. A single recess 288 can extend into all three surfaces 286a-c. It is thus appreciated that a single recess can extend into two or more adjacent outer surfaces of a bone fixation spike. Furthermore, the recess 288 extends from the tip 284 to the base 282. It should be appreciated that the recess 288 is further disposed and extends between the tip 284 and the base 282.

Referring now to FIGS. 13H-I, a bone fixation spike 290 is illustrated as including a base 292 and a tip 294 that is transversely spaced from the bone facing surface of the corresponding endplate in the manner described above. The bone fixation spike 290 includes six outer surfaces 296a-f that define a hexagon. The outer surfaces 296a-f converge along an outer transverse direction, and join at the tip 294. A recess 298 can extend into one or more, up to all of the outer surfaces 296a-f as illustrated.

Figure 14:
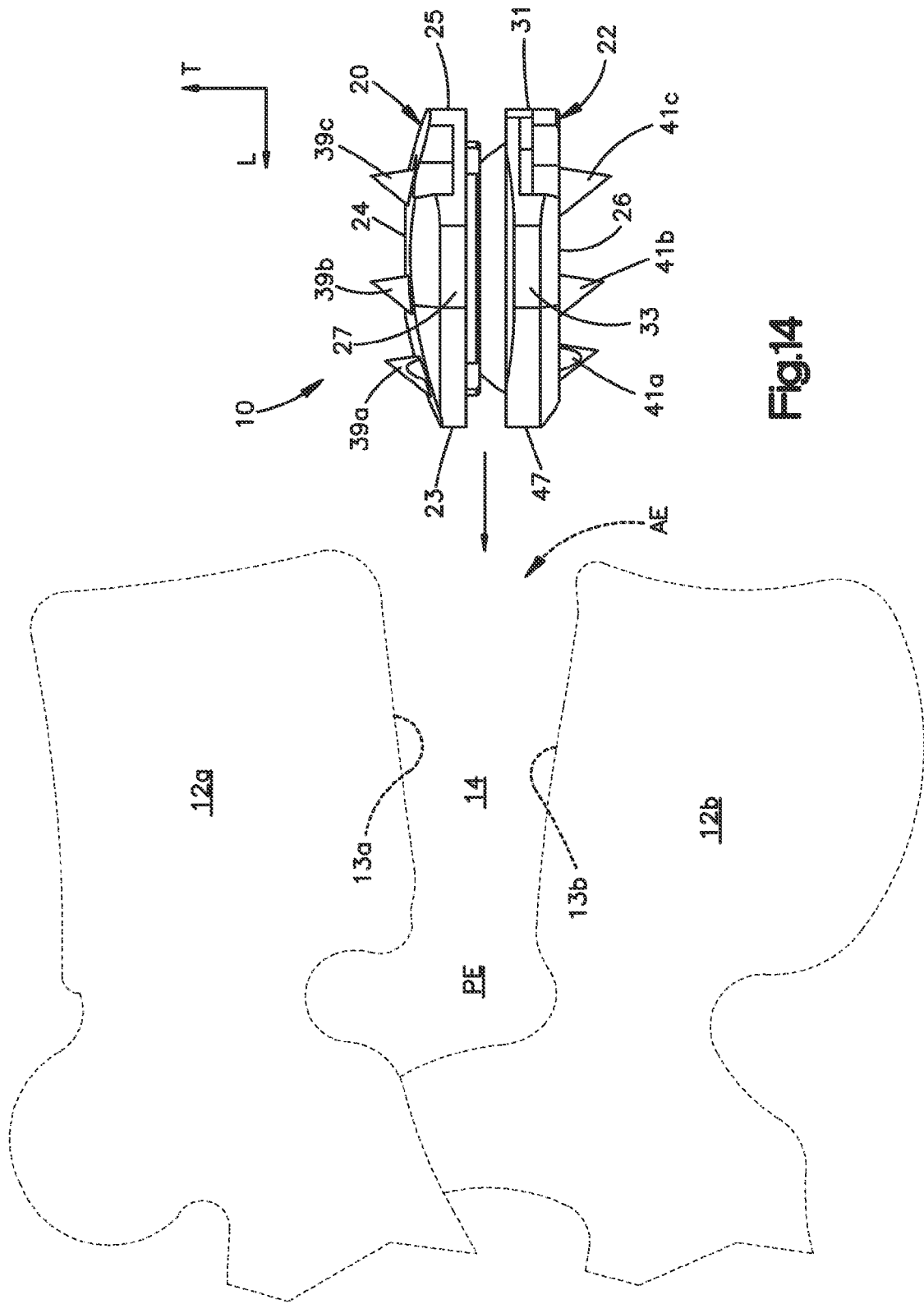
FIG. 14 is a side elevation view illustrating the insertion of the intervertebral implant illustrated in FIG. 2 into an intervertebral space.

Referring now to FIG. 14, during operation, the implant 10 is then aligned with the intervertebral space 14. The vertebral bodies 12a-b are retracted such that the anterior ends AE of the vertebral bodies are separated generally along the caudal-cranial dimension a distance greater than the posterior ends PE of the vertebral bodies 12a-b are separated. Thus, the intervertebral space 14 defines a caudal-cranial dimension at the anterior end AE that is greater than the caudal-cranial dimension of the intervertebral space 14 at the posterior end PE. Accordingly, the increase in height of the spikes 39 and 41 from the leading ends 23 and 47 toward the rear ends 25 and 31 of the endplates 20 and 22, respectively, correspond generally to an increase in height from the posterior end PE toward the anterior end AE of the intervertebral space 14.

It should be appreciated that the structure and features of the upper endplate 20 can be incorporated into the lower endplate 22, and the structure and features of the lower endplate 22 can be incorporated into the upper endplate 20. For instance, the shape of the bone facing surface 26 of the lower endplate 22 can be constructed as described with respect to the shape of the bone facing surface 24 of the upper endplate 20. Furthermore, the upper endplate 20 can carry the inlay 48 in the manner described with respect to the lower endplate 22, and the lower endplate 22 can carry the insert 44 in the manner described with respect to the upper endplate 20. Furthermore, one or more, up to all, of the spikes 39 of the upper endplate 20 can be constructed as described with respect to one or more, up to all, of the spikes 41 of the lower endplate 22. Likewise, one or more, up to all, of the spikes 41 of the lower endplate 22 can be constructed as described with respect to one or more, up to all, of the spikes 39 of the upper endplate 20.

As the implant 10 is inserted into the intervertebral space 14, the spikes 39 and 41 initially slide freely into the intervertebral space 14, and prior to full insertion begin to bite into the respective vertebral surfaces 13a-b. Thus, each spike 39 and 41 can leave a cutout or track in the respective vertebral surfaces 13a-b as the implant is increasingly inserted into the intervertebral space 14. Because the spikes 39 and 41 are laterally offset from each other, the spikes 39 and 41 do not ride in tracks created by forwardly disposed spikes and thus provide improved primary fixation. Once the implant 10 has been fully inserted into the intervertebral space 14, the retraction of the vertebral bodies 12a-b is released, thereby causing the surfaces 13a-b to return to their normal direction of extension, whereby the spikes 39 and 41 project into the surfaces 13a-b. The anterior spikes 39 and 41 project deeper into the surfaces 13a-b than the posterior spikes 39 and 41.

It is to be appreciated that the orthopedic implant 10 can be constructed as an intervertebral implant with any dimensions desirable for implantation of any intervertebral space along the spine, including but not limited to the cervical and lumbar regions. Furthermore, while the implant 10 is configured as a total disc replacement device, implants constructed in accordance with the teachings described herein are readily configurable for use with a range of bone-anchored orthopedic prostheses. For instance, the implant 10 can be configured as a spinal fusion implant, an intervertebral cage, spacer, or corpectomy device, long bone fixation plates and intramedullary nails and rods, bone fixation plates for fixation of craniomaxillofacial fractures, veterinary implants, and tips for guide wires.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

What is claimed is:

1. An intervertebral implant, comprising:
   an endplate defining a rear end, a front end spaced forward from the rear end, and laterally opposed sides that extend between the front and rear ends, the endplate defining an outer transverse bone facing surface configured to engage a respective adjacent vertebral surface, an inner surface opposite the outer transverse bone facing surface in a transverse direction, and a longitudinal axis that extends centrally between the laterally opposed sides from the rear end to the front end, wherein at least a portion of the endplate is made from a titanium;
   a joint member configured to be carried by the endplate, the joint member defining a rounded surface that is configured to provide an articulating joint with a rounded surface of a complementary joint member carried by a second endplate so as to allow for universal movement between the endplate and the second endplate, wherein at least a portion of the joint member is made from a cobalt chromium;
   a first bone fixation spike and a second bone fixation spike that each extend from the outer transverse bone facing surface and are disposed on opposite sides of the longitudinal axis,
   wherein 1) the endplate defines a recess that extends from a first end having a first portion that extends into the first bone fixation spike in the transverse direction and a second portion that extends into the outer transverse bone facing surface in the transverse direction, such that the recess terminates within the endplate at a second end that is disposed between the inner surface and the outer transverse bone facing surface, and 2) the first bone fixation spike and the outer transverse bone facing surface combine so as to define an enclosed perimeter of the first end of the recess.

2. The intervertebral implant as recited in claim 1, wherein i) the outer transverse bone facing surface is substantially smooth, ii) the endplate defines a substantially linear insertion direction into an intervertebral space, the insertion direction defined from the rear end toward the front end along a direction parallel to the longitudinal axis, such that the longitudinal axis defines substantially stationary orientation during insertion of the endplate into the intervertebral space; and iii) the first and second bone fixation spikes are spaced from each other along the substantially smooth outer transverse bone facing surface, each of the first and second bone fixation spikes projecting out from the outer transverse bone facing surface and having a base that is attached to outer transverse the bone facing surface, a substantially pointed outermost tip that is outwardly spaced from the outer transverse bone facing surface more than any other location of the bone fixation spike, and at least one outer surface that extends between the base and the outermost tip, the base defining a forwardmost end that is spaced from the outermost tip in the insertion direction, wherein the first recess extends into the outer transverse bone facing surface at a location between the outermost tip and the base, such that the at least one outer surface into which the recess extends faces at least partially forward, and the forwardmost end is spaced from the recess in the insertion direction.

3. The intervertebral implant as recited in claim 2, wherein at least one of the first and second bone fixation spikes defines a transverse axis extending between the outer transverse bone facing surface and the outermost tip, and the recess extends inwardly into the at least one outer surface toward the transverse axis.

4. The intervertebral implant as recited in claim 2, wherein the outermost tip is spaced from the outer transverse bone facing surface along the transverse direction that is perpendicular to the insertion direction, and the recess is arc shaped so as to define a partial cylindrical surface along an entirety of the transverse direction along which the recess extends.

5. The intervertebral implant as recited in claim 2, wherein the recess extends transversely from a location inwardly spaced from the outermost tip toward the base.

6. The intervertebral implant as recited in claim 2, wherein the first bone fixation spike is substantially pyramidal and includes three surfaces extending between the base and the outermost tip, and the recess extends into two of the three surfaces.

7. The intervertebral implant as recited in claim 2, wherein the recess of each does not extend into the forwardmost end, such that the first bone fixation spike is continuous from the outermost tip to the base along a direction that is at least partially defined by the insertion direction.

8. The intervertebral implant as recited in claim 1, wherein the joint member is threadedly connected to the endplate.

9. The implant as recited in claim 8, wherein the first and second bone fixation spikes are laterally staggered with respect to each other.

10. The implant as recited in claim 9, wherein the first and second bone fixation spikes are two of a plurality of bone fixation spikes, the plurality of bone fixation spikes comprises a longitudinally forward spike, a longitudinally rear spike, and a middle spike positioned longitudinally between the forward and rear spikes, wherein the forward spike is disposed laterally inward with respect to the middle and rear spikes, and the rear spike is disposed laterally between the front and middle spikes.

11. The implant as recited in claim 8, wherein the first and second bone fixation spikes are two of a plurality of bone fixation spikes, and the plurality of bone fixation spikes comprises a first group of bone fixation spikes, and a second group of bone fixation spikes constructed substantially identically with respect to the first group of bone fixation spikes, such that the second group of bone fixation spikes is symmetrical with respect to the first group of bone fixation spikes about the longitudinal axis.

12. The implant as recited in claim 11, wherein each of the plurality of bone fixation spikes projects out from the outer transverse bone facing surface and has a respective base that is attached to the outer transverse bone facing surface, a substantially pointed outermost tip that is outwardly spaced from the bone facing surface more than any other location of the bone fixation spike, at least one outer surface that extends between the base and the outermost tip, and a recess extending into at least one of the at least one outer surface at a location between the outermost tip and the base.

13. The intervertebral implant as recited in claim 1, wherein the endplate further defines a pocket that extends into the inner surface, and the joint member is configured to be inserted into the pocket such that the joint member is carried by the endplate.

14. The intervertebral implant as recited in claim 1, wherein the outer transverse bone facing surface defines a front section proximate the front end, a rear section proximate the rear end, and an intermediate section positioned forward of the rear end and rearward of the front end, and the outer transverse bone facing surface defines a length measured from the rear end forward to the front end, such that a first portion of the length measured from the rear end to the intermediate section is different than a second portion of the length measured from the intermediate section to the front end.

15. The intervertebral implant as recited in claim 1, wherein the outer transverse bone facing surface defines a front section proximate the front end, a rear section proximate the rear end, and an intermediate section positioned forward of the rear end and rearward of the front end, and the outer transverse bone facing surface is curved such that: 1) the outer transverse bone facing surface tapers towards the inner surface as the outer transverse bone facing surface extends away from the intermediate section and towards one of the laterally opposed sides, and 2) the outer transverse bone facing surface tapers towards the inner surface as the outer transverse bone facing surface extends away from the intermediate section and towards the other of the laterally opposed sides.

16. The implant as recited in claim 1, wherein, the endplate defines a height measured between the outer transverse bone facing surface and the inner surface in the transverse direction, and the height at the front end is different than the height at the rear end.

17. An implant comprising:
an upper endplate defining a first bone facing surface configured to engage an adjacent first vertebral surface, and an inner surface opposite the first bone facing surface in a transverse direction, the first bone facing surface defining a rear section, and a front section spaced forward from the rear section in a longitudinal direction which is perpendicular to the transverse direction, the first bone facing surface being curved such that: 1) the front section tapers toward the inner surface as the front section extends forward in the longitudinal direction, and 2) the rear section flares away from the inner surface as the rear section extends forward in the longitudinal direction, wherein at least a portion of the upper endplate is made from a titanium;

a first joint member configured to be carried by the upper endplate, the first joint member defining a rounded surface, wherein at least a portion of the first joint member is made from a cobalt chromium; and a lower endplate defining a second bone facing surface configured to engage an adjacent second vertebral surface, wherein the second bone facing surface is substantially planar and spaced from the first bone facing surface along the transverse direction, and each of the endplates defines a rear end and a front end spaced forward from the rear end along the longitudinal direction such that the front end is spaced from the rear end along a direction of insertion into an intervertebral space, the upper and lower endplates each further defining respective laterally opposed sides extending between the respective front and rear ends, the respective laterally opposed sides spaced from each other along a lateral direction that is perpendicular to both the longitudinal direction and the transverse direction, wherein at least a portion of the lower endplate is made from a titanium;

a second joint member configured carried by the lower endplate, the second joint member defining a rounded surface that is configured to provide an articulating joint with the rounded surface of the first joint member so as to allow for universal movement between the upper and lower endplates, wherein at least a portion of the second joint member is made from a cobalt chromium; and a plurality of bone fixation spikes spaced along the longitudinal direction, the bone fixation spikes projecting out from the first bone facing surface, wherein 1) each of the plurality of bone fixation spikes defines a footprint at the first bone facing surface from a view in the transverse direction, 2) each of the plurality of bone fixation spikes individually combines with the upper endplate to define a respective single cylindrical recess, such that each cylindrical recess is associated with only an individual one of the plurality of bone fixation spikes, each recess having a circular perimeter that is defined only by the respective individual one of the plurality of bone fixation spikes and the first bone facing surface, and 3) the circular perimeter has a center that is positioned at the first bone facing surface outside the footprint of the respective individual one of the plurality of bone fixation spikes.

18. The implant as recited in claim 17, wherein each of the plurality of bone fixation spikes defines a base, an outermost tip that is outwardly spaced from the first bone facing surface along the transverse direction, and a plurality of side walls that extend out between the base and the outermost tip, each of the plurality of bone fixation spikes defining a forwardmost end that is attached to the first bone facing surface such that each of the plurality of bone fixation spikes slopes rearward as it extends from the forwardmost end to the outermost tip, wherein the outermost tip of each of the plurality of bone fixation spikes has a transverse height with respect to a common horizontal plane, and the transverse height of the outermost tip of at least two of the plurality bone fixation spikes increases along the longitudinal direction from the front end of the first bone facing toward the rear end of the first bone facing surface, wherein the recess extends into at least a select one of the side walls, the recess open in a direction, the direction defined by one or both of the lateral and the longitudinal directions, along an entirety of its length from the base to a location disposed between the base and the outermost tip.

19. The implant as recited in claim 18, wherein the recess defines a length along a plane that is defined by the longitudinal and lateral directions, and the length at a location proximate to the outermost tip is less than the length at a location proximate to the base.

20. The implant as recited in claim 17, wherein the rounded surface of the first joint member is concave, and the rounded surface of the second joint member is convex.

21. The implant as recited in claim 20, wherein the first joint member is threadedly attached to the upper endplate.

22. The implant as recited in claim 20, wherein the lower endplate defines a pair of channels, and the second joint member includes a pair of guide wings that are insertable into the pair of channels, respectively, so as to attach the second joint member to the lower endplate.

23. The implant as recited in claim 17, wherein the front section is proximate the front end, the rear section is proximate the rear end, and an intermediate section is positioned forward of the rear end rearward of the front end, the first bone facing surface is curved such that the front section tapers toward the inner surface as the front section extends forward between the intermediate section and the front end, and the rear section flares away from the inner surface as the rear section extends forward between the rear section and the intermediate section.

* * * * *